(12) United States Patent
Sun

(10) Patent No.: US 12,060,281 B2
(45) Date of Patent: *Aug. 13, 2024

(54) COPPER NANOCLUSTERS, COMPOSITION COMPRISING THE SAME, AND TREATMENT OF MULTIPLE SCLEROSIS

(71) Applicant: Shenzhen Profound-View Pharma Tech Co., Ltd, Shenzhen (CN)

(72) Inventor: Taolei Sun, Wuhan (CN)

(73) Assignee: Shenzhen Profound-View Pharma Tech Co., Ltd, Shenzhen (CN)

( * ) Notice: Subject to any disclaimer, the term of this patent is extended or adjusted under 35 U.S.C. 154(b) by 576 days.

This patent is subject to a terminal disclaimer.

(21) Appl. No.: 17/309,744

(22) PCT Filed: Jun. 28, 2019

(86) PCT No.: PCT/CN2019/093463
§ 371 (c)(1),
(2) Date: Jun. 16, 2021

(87) PCT Pub. No.: WO2020/147268
PCT Pub. Date: Jul. 23, 2020

(65) Prior Publication Data
US 2021/0379101 A1    Dec. 9, 2021

(30) Foreign Application Priority Data

Jan. 16, 2019 (WO) ............... PCT/CN2019/071901

(51) Int. Cl.
| | | |
|---|---|---|
| A61K 9/14 | (2006.01) | |
| A61K 33/34 | (2006.01) | |
| A61K 47/54 | (2017.01) | |
| A61K 47/61 | (2017.01) | |
| A61K 47/64 | (2017.01) | |
| A61K 47/69 | (2017.01) | |
| A61P 25/16 | (2006.01) | |
| A61P 25/28 | (2006.01) | |
| C01G 3/00 | (2006.01) | |
| C08L 5/08 | (2006.01) | |
| B82Y 5/00 | (2011.01) | |
| B82Y 30/00 | (2011.01) | |
| B82Y 40/00 | (2011.01) | |

(52) U.S. Cl.
CPC ............... *C01G 3/006* (2013.01); *A61K 9/14* (2013.01); *A61K 33/34* (2013.01); *A61K 47/54* (2017.08); *A61K 47/542* (2017.08); *A61K 47/545* (2017.08); *A61K 47/61* (2017.08); *A61K 47/64* (2017.08); *A61K 47/6923* (2017.08); *A61P 25/16* (2018.01); *A61P 25/28* (2018.01); *C08L 5/08* (2013.01); *B82Y 5/00* (2013.01); *B82Y 30/00* (2013.01); *B82Y 40/00* (2013.01); *C01P 2004/04* (2013.01); *C01P 2004/64* (2013.01)

(58) Field of Classification Search
CPC .......... C01G 3/006; A61K 9/14; A61K 33/34; A61K 47/54; A61K 47/542; A61K 47/545; A61K 47/61; A61K 47/64; A61K 47/6923; A61K 47/62; A61K 47/6929; A61K 31/787; A61P 25/16; A61P 25/28; A61P 27/06; C08L 5/08; B82Y 5/00; B82Y 30/00; B82Y 40/00; C01P 2004/04; C01P 2004/64; B22F 1/102; B22F 1/054; G01N 33/5308; G01N 33/523; G01N 33/84

See application file for complete search history.

(56) References Cited

U.S. PATENT DOCUMENTS

| | | | | |
|---|---|---|---|---|
| 2016/0271175 | A1* | 9/2016 | Warner | ............... C07C 59/105 |
| 2021/0379199 | A1* | 12/2021 | Sun et al. | ............. C07C 59/105 |

FOREIGN PATENT DOCUMENTS

| | | |
|---|---|---|
| CN | 104458050 | 3/2015 |
| CN | 105834444 | 8/2016 |
| EP | 3449945 | 3/2019 |
| EP | 3545948 | 10/2019 |
| WO | 2014125256 | 8/2014 |
| WO | 2020147029 | 7/2020 |

OTHER PUBLICATIONS

Baghdasaryan et al., Copper nanoclusters: designed synthesis, structural diversity, and multiplatform applications. Nanoscale, 2021, 13, 6283-6340 | 6283. (published Feb. 26, 2021) (Year: 2021).*
Beitollahi et al., Application of a Modified CuO Nanoparticles Carbon Paste Electrode for Simultaneous Determination of Isoperenaline, Acetaminophen and N-acetyl-L-cysteine. Electroanalysis 2016, 28, 645-653 (Year: 2016).*
Mlakar et al., (Mlakar et al., A Electrochemical Characterization of Biochemically Active Cu(II) Mixed Ligand Complex with Histidine and Cysteine. Electroanalysis 2017, 29, 392-397) (Year: 2017).*
Stadelmann, Multiple sclerosis as a neurodegenerative disease: pathology, mechanisms and therapeutic implications, Opin Neurol 24:224-229 (Year: 2011).*
Beitollahi et al., Application of a Modified CuO Nanoparticles Carbon Paste Electrode for Simultaneous Determination of Isoperenaline, Acetaminophen and N-acetyl-L-cysteine. Electroanalysis 2016, 28, 645 â 653.*
Mlakar et al., Electrochemical Characterization of Biochemically Active Cu(II) Mixed Ligand Complex with Histidine and Cysteine. Electroanalysis 2017, 29, 392 â 397.*
Adamczyk B, et al. New Insights into the Role of Oxidative Stress Mechanisms in the Pathophysiology and Treatment of . . . Oxid Med Cell Longev. 2016:1973834. Epub Oct. 18, 2016.
Jin R, et al. Atomically Precise Colloidal Metal Nanoclusters and Nanoparticles: Fundamentals and Opportunities, Chem. Rev., 2016, 116, 10346-10413.

(Continued)

Primary Examiner — Robert A Wax
Assistant Examiner — Ngoc-Anh Thi Nguyen
(74) Attorney, Agent, or Firm — Yihe Intellectual Property Services Co. Ltd

(57) ABSTRACT

Treatment of multiple sclerosis with copper nanoclusters (CuNCs).

10 Claims, 25 Drawing Sheets

(56) References Cited

OTHER PUBLICATIONS

Kim GH, et al. The Role of Oxidative Stress in Neurodegenerative Diseases, Exp Neurobiol. 2015, 24(4): 325-340.
Liu X, et al. Atomically Precise Copper Nanoclusters and Their Applications, Coord. Chem. Rev., 2018, 359, 112-126.
Ohl K, et al. Oxidative stress in multiple sclerosis: Central and peripheral mode of action. Exp Neurol. 2016; 277:58-67.
Yao Q, et al. Toward Total Synthesis of Thiolate-Protected Metal Nanoclusters, Acc. Chem. Res.; 2018; 51; 1338-1348.
Borghei et al. (2017) Novel fluorometric assay for detection of cysteine as a reducing agent and template in formation of copper nanoclusters. J Fluoresc. 27: 529-536.
Gao et al. (2019) Gold nanoclusters for Parkinson's disease treatment. Biomaterials. 194: 36-46.
Hao et al. (2019) Chiral molecule-mediated porous CuxO nanoparticle clusters with antioxidation activity for ameliorating Parkinson's disease. J. Am. Chem. Soc. 141, 1091-1099.
Hung et al. (2012) The hypoxia imaging agent CuII(atsm) is neuroprotective and improves motor and cognitive functions in multiple animal models of Parkinson's disease. JEM. 209, 837-854.
Manna U, et al. Layer-by-layer self-assembly of modified hyaluronic acid/chitosan based on hydrogen bonding. Biomacromolecules. 2009; 10: 2632-9.
Ojha et al. A review on nanotechnology based innovations in diagnosis and treatment of multiple sclerosis. Journal of cellular immunotherapy. 2018; 4: 56-64.
Ohl et al. Oxidative stress in multiple sclerosis: central and peripheral mode of action. Experimental Neurology. 2016; 277: 58-67.
Sheykhansari et al. Redox metals homeostasis in multiple sclerosis and amyotrophic lateral sclerosis: a review. Cell Death and Disease. 2018; 9: 348.
Singh. Recent trends in nano-biotechnology reinforcing contemporary pharmaceutical design. Current Pharmaceutical Design. 2016, 22: 1415.

\* cited by examiner (i)

(a)

(b)

(c)

(d)

(i)

(j)

(a)

(b)          (c)

(a)

COPPER NANOCLUSTERS, COMPOSITION COMPRISING THE SAME, AND TREATMENT OF MULTIPLE SCLEROSIS

FIELD OF THE INVENTION

The present invention relates to copper nanoclusters (CuNCs), compositions comprising CuNCs, and their applications in treatment of multiple sclerosis (MS).

BACKGROUND OF THE INVENTION

Multiple sclerosis (MS) is a multifactorial disease of the central nervous system (CNS) characterized by an inflammatory process and demyelination. MS is an autoimmune disease directed against myelin basic protein (MBP), proteolipid protein (PLP), and/or myelin oligodendrocyte glycoprotein (MOG). The etiology of the disease is still not fully understood. Accumulating evidence suggests that oxidative stress (OS) plays a major role in the pathogenesis of multiple sclerosis (MS). Reactive oxygen species (ROS), which if produced in excess lead to oxidative stress, have been implicated as mediators of demyelination and axonal damage in both MS and its animal models. In the acute phase OS initiates inflammatory processes and in the chronic phase it sustains neurodegeneration. Redox processes in MS are associated with mitochondrial dysfunction, dysregulation of axonal bioenergetics, iron accumulation in the brain, impaired oxidant/antioxidant balance, and OS memory. OS at each stage of MS is a key element in the pathogenesis of the disease. At the time of relapse all these processes are intensified, leading to the loss of neurons over years (Adamczyk 2016; Ohl 2016).

Current treatment is focused on decreasing inflammation, however only partially on preventing neurodegeneration. The course of the disease is affected by the use of antioxidants and substances that affect antioxidant pathways which reduced the severity and cause faster remission and less pronounced course of neuroinflammation and neurodegeneration. Antioxidants are substances that protect the body against free radicals; antioxidants can be enzymatic or nonenzymatic. Among the enzymes the most important include catalase (CAT), glutahione peroxidase (GPx), superoxide dismutase (SOD) (Adamczyk 2016).

Copper nanoclusters (CuNCs) are a kind of substances in between copper atom and copper nanocrystals. They are composed of several to dozens of copper atoms with stabilizing ligands on the surface (Yao 2018). CuNCs have attracted considerable attention owing to their unique size-dependent optical and electronic properties and thus exhibit great potentials in a wide range of applications, e.g. nanocatalysts, biosensors, cellular labeling, and optoelectronic nanodevices (Jin 2016; Liu 2018). To the best of our knowledge, applying CuNCs for the treatment of MS has not be reported before.

SUMMARY OF THE INVENTION

The present invention provides the use of copper nanoclusters (CuNCs) for manufacture of a medicament for the treatment of multiple sclerosis in a subject, wherein said CuNCs comprise a ligand.

In certain embodiments for the manufacture use, the ligand-modified CuNCs have a diameter in the range of 0.5-3 nm.

In certain embodiments for the manufacture use, the ligand-modified CuNCs have a diameter in the range of 0.5-2.5 nm.

In certain embodiments for the manufacture use, the ligand is one selected from the group consisting of thymine, thymine-modified hyaluronic acid (TMHA), L-cysteine and its derivatives, D-cysteine and its derivatives, cysteine-containing oligopeptides and their derivatives, and other thiol-containing compounds.

In certain embodiments for the manufacture use, the L-cysteine and its derivatives are selected from the group consisting of L-cysteine, N-isobutyryl-L-cysteine (L-NIBC), and N-acetyl-L-cysteine (L-NAC), and wherein the D-cysteine and its derivatives are selected from the group consisting of D-cysteine, N-isobutyryl-D-cysteine (D-NIBC), and N-acetyl-D-cysteine (D-NAC).

In certain embodiments for the manufacture use, the cysteine-containing oligopeptides and their derivatives are cysteine-containing dipeptides, cysteine-containing tripeptides or cysteine-containing tetrapeptides.

In certain embodiments for the manufacture use, the cysteine-containing dipeptides are selected from the group consisting of L-cysteine-L-arginine dipeptide (CR), L-arginine-L-cysteine dipeptide (RC), L-histidine-L-cysteine dipeptide (HC), and L-cysteine-L-histidine dipeptide (CH).

In certain embodiments for the manufacture use, the cysteine-containing tripeptides are selected from the group consisting of glycine-L-cysteine-L-arginine tripeptide (GCR), L-proline-L-cysteine-L-arginine tripeptide (PCR), L-lysine-L-cysteine-L-proline tripeptide (KCP), and L-glutathione (GSH).

In certain embodiments for the manufacture use, the cysteine-containing tetrapeptides are selected from the group consisting of glycine-L-serine-L-cysteine-L-arginine tetrapeptide (GSCR), and glycine-L-cysteine-L-serine-L-arginine tetrapeptide (GCSR).

In certain embodiments for the manufacture use, the other thiol-containing compounds are selected from the group consisting of 1-[(2S)-2-methyl-3-thiol-1-oxopropyl]-L-proline, thioglycollic acid, mercaptoethanol, thiophenol, D-3-trolovol, N-(2-mercaptopropionyl)-glycine, and dodecyl mercaptan.

The present invention provides the use of copper nanoclusters (CuNCs) to treat a subject with multiple sclerosis, wherein said CuNCs comprise a ligand.

In certain embodiments for the treatment use, the ligand-modified CuNCs have a diameter in the range of 0.5-3 nm.

In certain embodiments for the treatment use, the ligand-modified CuNCs have a diameter in the range of 0.5-2.5 nm.

In certain embodiments for the treatment use, the ligand is one selected from the group consisting of thymine, thymine-modified hyaluronic acid (TMHA), L-cysteine and its derivatives, D-cysteine and its derivatives, cysteine-containing oligopeptides and their derivatives, and other thiol-containing compounds.

In certain embodiments for the treatment use, the L-cysteine and its derivatives are selected from the group consisting of L-cysteine, N-isobutyryl-L-cysteine (L-NIBC), and N-acetyl-L-cysteine (L-NAC), and wherein the D-cysteine and its derivatives are selected from the group consisting of D-cysteine, N-isobutyryl-D-cysteine (D-NIBC), and N-acetyl-D-cysteine (D-NAC).

In certain embodiments for the treatment use, the cysteine-containing oligopeptides and their derivatives are cysteine-containing dipeptides, cysteine-containing tripeptides or cysteine-containing tetrapeptides.

In certain embodiments for the treatment use, the cysteine-containing dipeptides are selected from the group consisting of L-cysteine-L-arginine dipeptide (CR), L-arginine-L-cysteine dipeptide (RC), L-histidine-L-cysteine dipeptide (HC), and L-cysteine-L-histidine dipeptide (CH).

In certain embodiments for the treatment use, the cysteine-containing tripeptides are selected from the group consisting of glycine-L-cysteine-L-arginine tripeptide (GCR), L-proline-L-cysteine-L-arginine tripeptide (PCR), L-lysine-L-cysteine-L-proline tripeptide (KCP), and L-glutathione (GSH).

In certain embodiments for the treatment use, the cysteine-containing tetrapeptides are selected from the group consisting of glycine-L-serine-L-cysteine-L-arginine tetrapeptide (GSCR), and glycine-L-cysteine-L-serine-L-arginine tetrapeptide (GCSR).

In certain embodiments for the treatment use, the other thiol-containing compounds are selected from the group consisting of 1-[(2S)-2-methyl-3-thiol-1-oxopropyl]-L-proline, thioglycollic acid, mercaptoethanol, thiophenol, D-3-trolovol, N-(2-mercaptopropionyl)-glycine, and dodecyl mercaptan.

The objectives and advantages of the invention will become apparent from the following detailed description of preferred embodiments thereof in connection with the accompanying drawings.

DESCRIPTION OF THE DRAWINGS

Preferred embodiments according to the present invention will now be described with reference to the Figures, in which like reference numerals denote like elements.

FIG. 1(a)(ii) illustrates the synthesis of TMHA, and FIG. 1(a)(iii) and (iv) show the typical appearance of HA and TMHA respectively.

FIGS. 4(a) and (d) show the TEM or AFM images of TMHA-liganded CuNCs prepared by TMHA with 3.2% DS of thymine respectively; FIGS. 4(b) and (e) show the TEM or AFM images of TMHA-liganded CuNCs prepared by TMHA with 10.5% DS of thymine respectively; FIGS. 4(c) and (f) show the TEM or AFM images of TMHA-liganded CuNCs prepared by TMHA with 20.1% DS of thymine respectively; FIGS. 4(g) and (h) show the MS spectra of TMHA or TMHA-liganded CuNCs respectively; and FIGS. 4 (i) and (j) show XPS spectra of (i) full region of CuNCs and (j) Cu 2p region. In FIG. 4, insets: (b, g, h) schematic illustration of TMHA-liganded CuNCs nanowires, ionization fragments and TMHA-liganded CuNCs, respectively; (e, f) isolated CuNCs that are composed of nanowires.

DETAILED DESCRIPTION OF THE EMBODIMENTS

Figure 1:
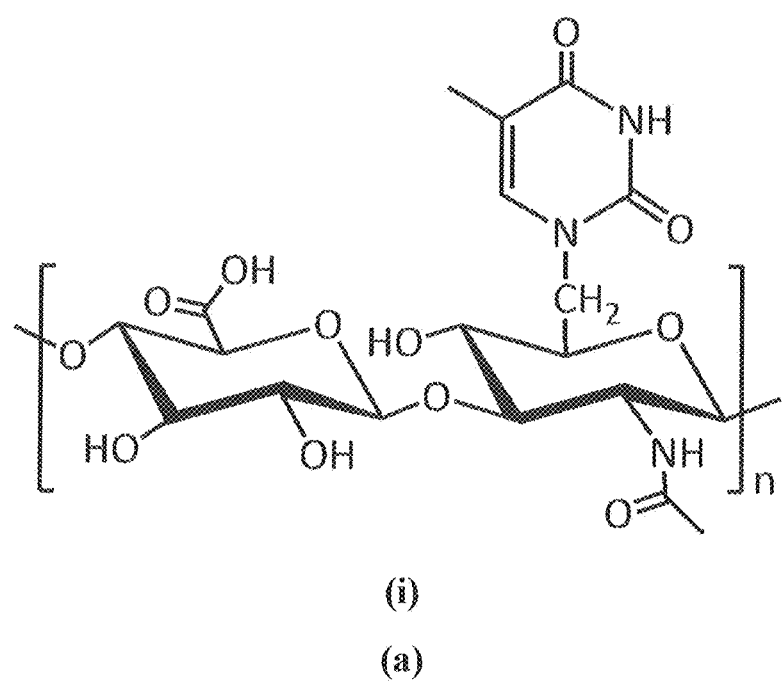
FIG. 1(a)(i) shows the structure of TMHA represented by Formula 1.
FIG. 1(b) shows UV-vis spectra of TMHA (red line) and pure HA (blue line), respectively.
FIG. 1(c) shows FT-IR of HA and TMHA.
FIG. 1(d) shows $^1$H NMR spectra of HA and TMHA.
Figure 1:
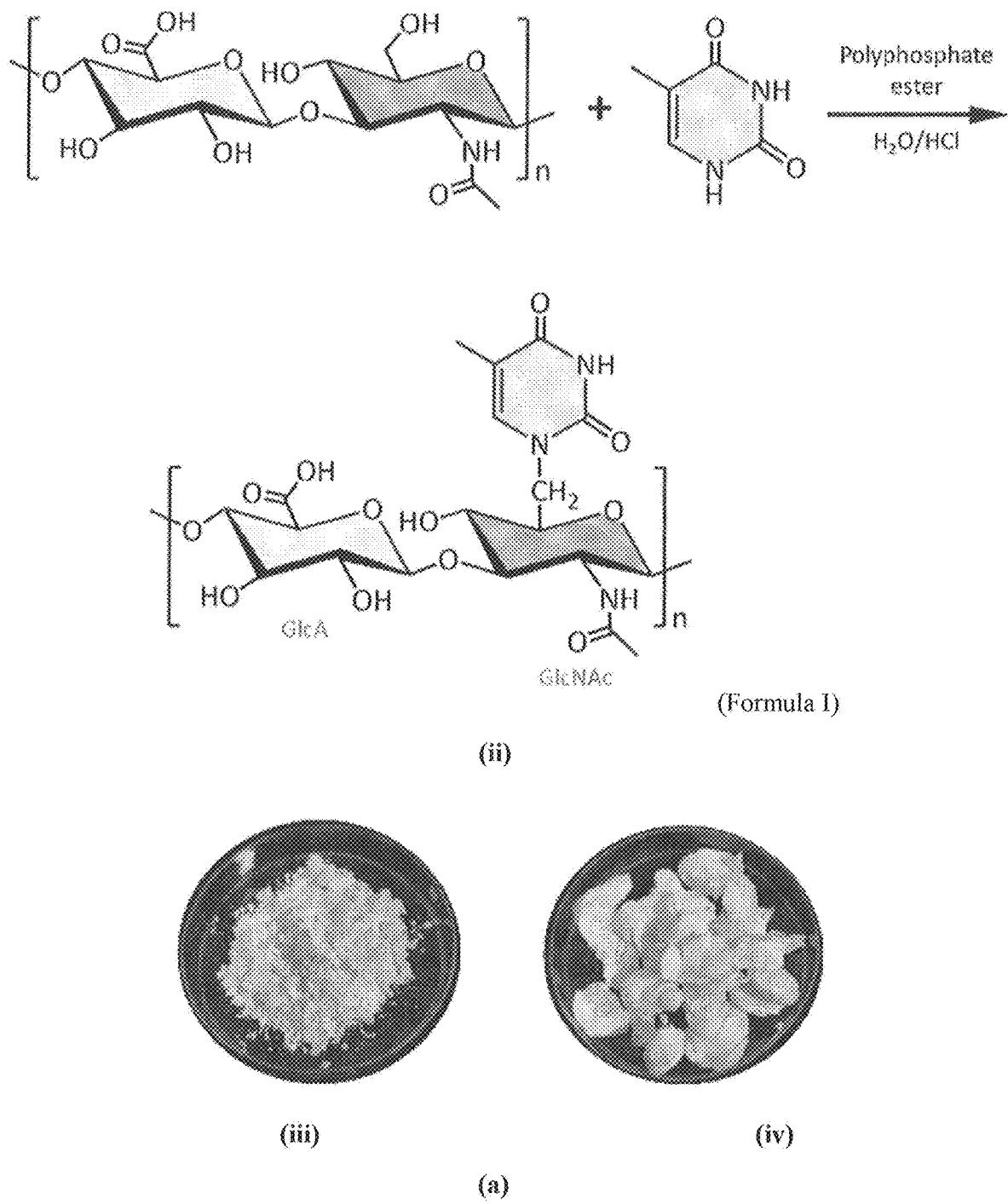
Figure 1:
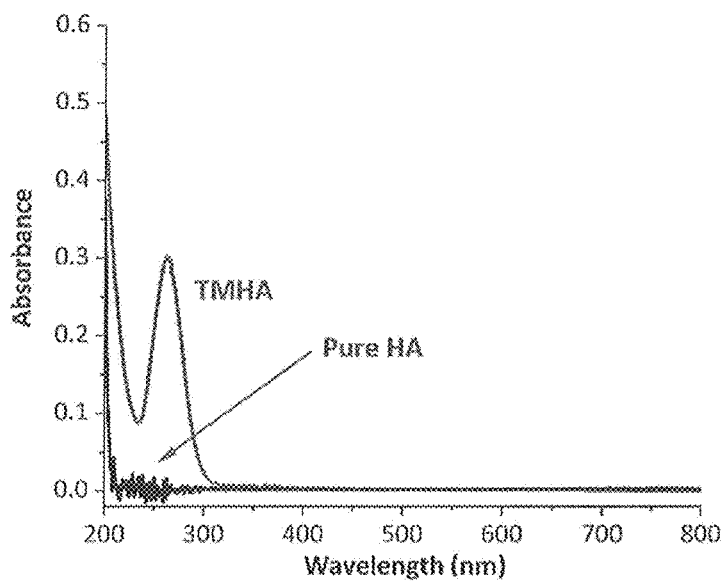
Figure 1:
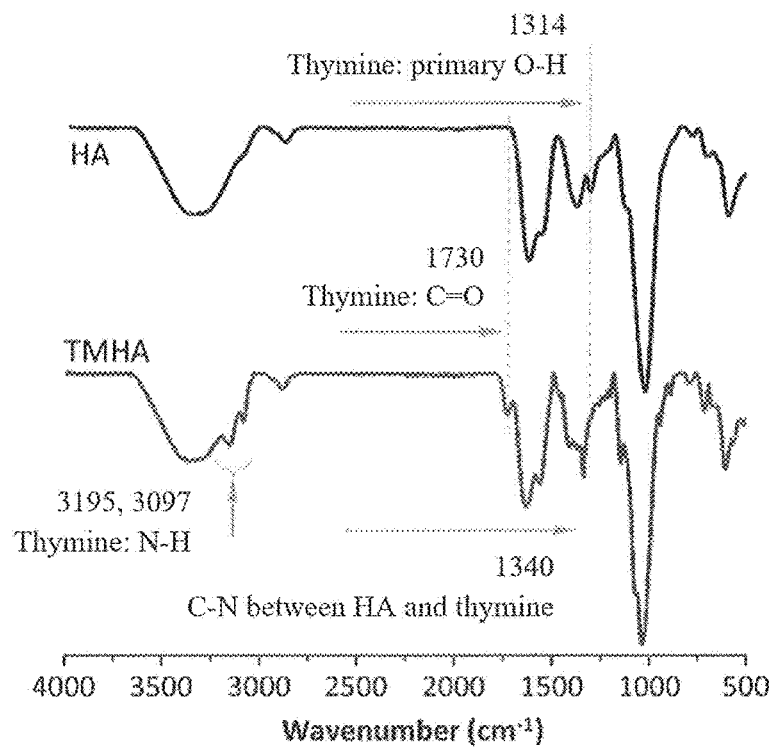
Figure 1:
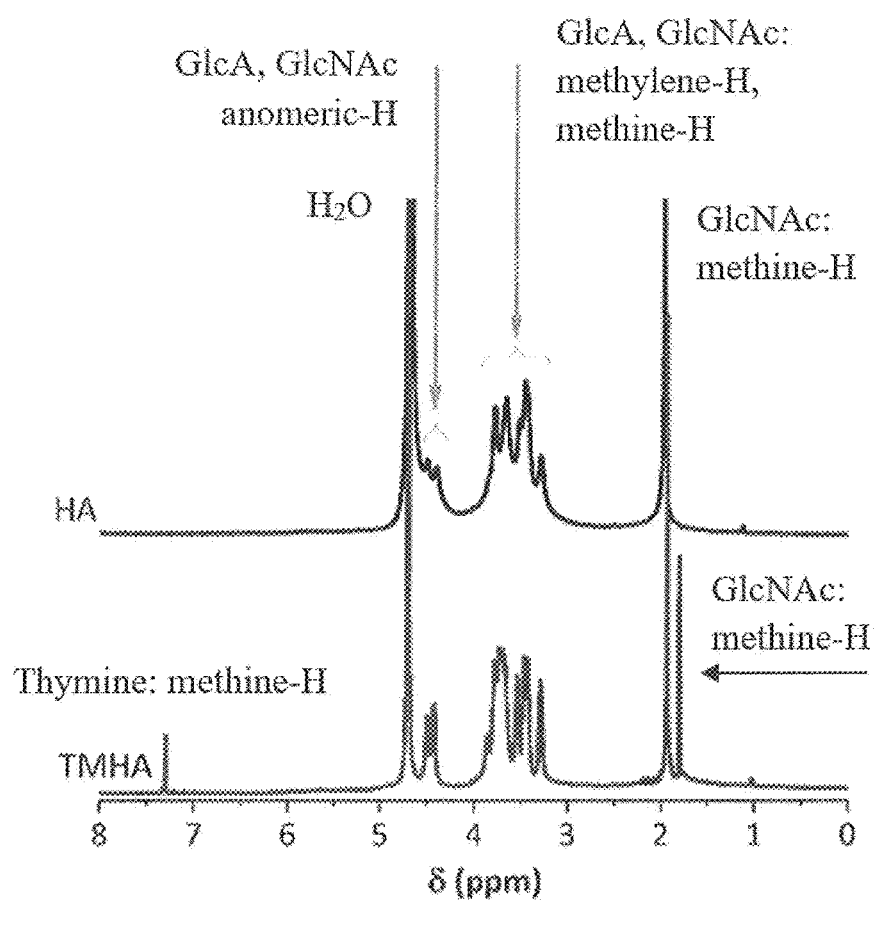

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

Superoxide dismutase (SOD) plays a significant role in catalyzing the breakdown of highly reactive $O_2^-$ to less reactive $H_2O_2$ and oxygen. Cytosolic copper/zinc-SOD (SOD1), mitochondrial manganese SOD (SOD2), and extracellular SOD (SOD3) are three distinct isoforms of SOD that have been identified. SOD1 and SOD2 are mainly involved in the elimination of $O_2^-$ in the cytosol and mitochondria, respectively (Kim 2015).

Glutathione peroxidases (GPX) contain a family of multiple isoenzymes which catalyze the reduction of $H_2O_2$ and lipid peroxides utilizing glutathione (GSH) as an electron donor. GPX is located in both cytosol and mitochondria. In mammals, there are five different isoforms of selenium-dependent glutathione peroxidases (GPX1-4 and 6) and three non-selenium congeners (GPX 5, 7 and 8) that have cysteine instead of selenocysteine. Antioxidant function of GPXs depends on each isoform and location in the cells; GPX1 has been regarded as one of the major antioxidant enzymes in the brain. Studies have suggested that upregulation of GPX1 could be one of the protective responses against neuronal injury (Kim 2015).

Catalase is responsible for the conversion of $H_2O_2$ to water and oxygen using either iron or manganese as a cofactor. Catalase is located in peroxisomes and also found in the cytoplasm and mitochondria. The role of catalase is minor at low levels of $H_2O_2$, but becomes increasingly important at higher levels of $H_2O_2$(Kim 2015).

In normal organisms, reactive oxygen species (ROS) maintains homeostasis through regulation of various enzymes. Catalase (CAT) is present in almost all living organisms. CAT is an enzymatic scavenger, a contact enzyme based on iron porphyrin. It promotes the decomposition of $H_2O_2$ into molecular oxygen and water and is one of the key enzymes in the biological defense system. Glutathione peroxidase (GPx) is an important peroxide-degrading enzyme widely present in the body. The active center of GPx is selenocysteine. Selenium is a component of the GPx enzyme system, which catalyzes the conversion of GSH to GSSG, and reduces toxic peroxides to non-toxic hydroxy compounds, thereby protecting the structure and function of cell membranes from interference and damage by peroxides. Superoxide dismutase (SOD) is a naturally occurring superoxide radical scavenger in the body that converts harmful superoxide radicals into hydrogen peroxide. Although hydrogen peroxide is still a harmful oxygen to the body, peroxidase in the body immediately breaks it down into completely harmless water. CAT is known to be responsible for the removal of excess $H_2O_2$ during oxidative stress, but GPx can fine tune the concentration of $H_2O_2$ in cellular signals. It has been reported that CAT-GPx synergy is important for the correct control of $H_2O_2$ levels under pathophysiological conditions. In this way, the three enzymes form a complete antioxidant chain.

The present invention provides compositions and methods for treating neurodegenerative diseases that are initiated or accelerated by the oxidative stress (OS) caused by reactive oxygen species (ROS). The neurodegenerative diseases include, but not limited to, Alzheimer's disease (AD), Parkinson's disease (PD), Huntington's disease (HD), amyotrophic lateral sclerosis (ALS), spinocerebellar ataxia (SCA), and glaucoma.

The present invention provides copper nanoclusters (CuNCs) modified with one or more ligands. In certain embodiments, the ligand-modified CuNCs have a diameter in the range of 0.5-5 nm, preferably in the range of 0.5-3 nm, and more preferably in the range of 0.5-2.5 nm. In certain embodiments, the ligands include, but not limited to, thymine, thymine-modified hyaluronic acid (TMHA), L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptan.

The present invention provides a composition for treating a subject with multiple sclerosis. In certain embodiments, the composition comprises copper nanoclusters (CuNCs), and a pharmaceutically acceptable excipient.

In certain embodiments, the composition comprises thymine-modified hyaluronic acid (TMHA), and a pharmaceutically acceptable excipient.

In certain embodiments, the composition comprises TMHA-liganded CuNCs, and a pharmaceutically acceptable excipient.

The present invention provides use of copper nanoclusters (CuNCs) to manufacture a medication for treatment of MS.

The present invention provides use of thymine-modified hyaluronic acid (TMHA) to manufacture a medication for treatment of MS.

The present invention provides use of TMHA-liganded CuNCs to manufacture a medication for treatment of MS.

The present invention provides a process for treating a subject with MS.

In certain embodiments, the process comprises: administering to the subject an effective dosage of a composition comprising copper nanoclusters (CuNCs).

In certain embodiments, the process comprises: administering to the subject an effective dosage of a composition comprising thymine-modified hyaluronic acid (TMHA).

In certain embodiments, the process comprises: administering to the subject an effective dosage of a composition comprising TMHA-liganded CuNCs.

In certain embodiments, the subjects with MS are administered an effective amount of CuNCs by intraperitoneal injection. In certain embodiments, the subjects with MS are administered an effective amount of TMHA by intraperitoneal injection. In certain embodiments, the subjects with MS are administered an effective amount of TMHA-liganded CuNCs by intraperitoneal injection. In certain embodiments, the effective amounts are in the range of 2-100 mg $kg^{-1}$.

The present invention provides thymine-modified hyaluronic acid (TMHA) and a process of synthesizing TMHA.

The structure of TMHA is represented by Formula 1 as shown in FIG. 1(a)(i), where the HA is composed of glucuronic acid (GlcA)-N-acetylglucosamine (GlcNAc) repeats, the GlcNAc is modified by thymine, and n is an integer, from 10-10,000, preferably 10-1,000, more preferably 10-100. It is to be noted that not every single GlcNAc in the HA is modified by a thymine. The degree of substitution (DS) of thymine in TMHA is defined as the number of thymine molecules per 100 sugar residues of TMHA. The degree of substitution (DS) of thymine in TMHA is in the range of 1-50%, further to 4-30%, yet further to 5-20%, yet further to 7-16%, and yet further to 8-15%.

The process of synthesizing TMHA comprises:

providing an acidic aqueous solution of thymine in a concentration of 0.05-0.02 w/v %; in certain embodiments, the acidic aqueous solution is composed of water and HCl;

providing an HA solution in a concentration of 1-5 wt %;

adding a catalyst into the HA solution; in certain embodiments, the catalyst is polyphosphate ester;

adding the acidic aqueous solution of thymine into the catalyst-containing HA solution to form an HA-thymine mixture; in certain embodiments, the acidic aqueous solution of thymine is added by dropwise injection;

heating the HA-thymine mixture for a predetermined period; in certain embodiments, the heating is at 45-50° C. for a period of 12-20 hours in an oil-bath;

cooling the heated HA-thymine mixture to a predetermine temperature; in certain embodiments, the predetermined temperature is about 0° C. to precipitate unreacted thymine;

dialyzing supernatant solution from the cooled HA-thymine mixture; in certain embodiments, the dialysis is performed for 48-96 hours with molecular weight cut off 8000 to remove the unreacted reagents and impurities; and lyophilizing the dialyzed solution to obtain TMHA.

The present invention also provides TMHA-liganded CuNCs and a process of synthesis of TMHA-liganded CuNCs.

In certain embodiments, the process of TMHA-liganded CuNCs synthesis comprises:

providing a TMHA solution; in certain embodiments, the TMHA solution is 0.1 mM, pH7.0;

adding $CuSO_4$ solution into the TMHA solution; in certain embodiments, the $CuSO_4$ solution is 20 mM, pH7.0, and were added dropwise;

thereby allowing the mixture to react; in certain embodiments, the reaction is for 20 minutes in dark at 37° C. to obtain the TMHA-liganded CuNCs solution; the TMHA-liganded CuNCs solution is stored in dark at 4° C. for use.

Under radiation of UV-light (365 nm), a bright orange-red emission is clearly visible, indicating successful formation of luminescent CuNCs.

In certain embodiments, the molar ratio between Cu and TMHA is in the range of 10:1 to 500:1, further in the range of 15:1 to 300:1, yet further in the range of 20:1 to 200:1, yet further in the range of 25:1 to 100:1, and yet further in the range of 30:1 to 80:1.

The TMHA-liganded CuNCs contains well dispersed spherical nanoclusters with diameters of 0.5-3 nm.

The following examples are provided for the sole purpose of illustrating the principles of the present invention; they are by no means intended to limit the scope of the present invention.

EXAMPLES (1) Synthesis of Thymine Modified Hyaluronic Acid (TMHA)

First, polyphosphate ester as a catalyst was prepared. Diethyl ether (14.5 mL) and $CHCl_3$ (5.6 mL) were added to phosphorus pentoxide (10 g) with stirring, and the mixture was heated under reflux for 12 h at 50° C. to obtain a clear solution. After cooling down to room temperature, the solvent was distilled off under vacuum. The resultant colorless viscous residue was polyphosphate ester and used as a catalyst without further purification.

Second, the TMHA was synthesized as follows. A clear solution of thymine (23.6 mg) was obtained by dissolving in 25 mL of $H_2O$ with the addition of 0.25 mL of concentrated HCl solution (25%). Polyphosphate ester (1.5 g) was added to HA solution (50 mL, 2.2 wt %; MW120KD), followed by dropwise injection of thymine, and the mixture was heated to 50° C. for 16 h in an oil-bath and cooled down to 0° C. to precipitate unreacted thymine. Then, the supernatant solution was dialyzed for 72 h via a dialysis bag (molecular weight cut off 8000) to remove any unreacted reagents and impurities. The resultant solution was lyophilized to obtain TMHA; the yield was 86%, and the degree of substitution (DS) was 10.5%. The quality of final product was characterized by $^1H$ NMR and FT-IR.

Referring now to FIG. 1, FIG. 1(a)(ii) illustrates the synthesis of TMHA, and FIG. 1(a)(iii) and (iv) show the typical appearance of HA and TMHA respectively; FIG. 1(b) shows UV-vis spectra of TMHA (red line) and pure HA (blue line), respectively; FIG. 1(c) shows FT-IR of HA and TMHA; and FIG. 1(d) shows $^1H$ NMR spectra of HA and TMHA. The $^1H$ NMR spectra were carried out in $D_2O$ at 80° C. and 400 MHz at a sample concentration of 10 mg mL$^{-1}$. For FTIR analysis, KBr crystals were used as the matrix during sample preparation.

The chemical structure of TMHA conjugate was qualitatively studied by FTIR in virtue of comparing the spectra of native HA and those of its derivatives. These spectra displayed significant differences in the range of 3000-3200 cm$^{-1}$ and 1300-1800 cm$^{-1}$ compared to that of the native HA, especially to the TMHA derivatives with higher DS. Characteristic peaks assignments of the native HA were 3360 cm$^{-1}$ (secondary 0-H stretch), 2873 cm$^{-1}$ (C—H stretch), 1622 cm$^{-1}$ (amide II band, C—O stretch of acetyl group), 1554 cm$^{-1}$ (amide II band, N—H stretch), 1380 cm$^{-1}$ (asymmetric C—H stretch bending of CH2 group), 1314 cm$^{-1}$ (O—H stretch of primary alcoholic group), and 1026 cm$^{-1}$ (skeletal vibration involving the bridge C—O stretch). The spectrum of TMHA derivatives displayed three characteristic peaks, i.e., 3195 and 3079 cm$^{-1}$ (N—H stretch), 1730 cm$^{-1}$ (C=O stretch), and 1340 cm$^{-1}$ (C—N stretching vibration), hinting the functionalization of HA by thymine. More importantly, the disappearance of a band at 1314 cm$^{-1}$, which was ascribed to the O—H stretch of primary alcoholic group belonging to HA, suggested the reaction mechanism that only the primary —OH group of GlcNAc of HA reacted with thymine. The successful modification was further confirmed by $^1H$ NMR analysis.

(2) Synthesis of TMHA-Liganded CuNCs with TMHA 10 mL of TMHA (DS of 10.5%) solution (0.1 mM, pH 7.0) was gradually heated up to 37° C. to dissolve the TMHA. 2 mL of $CuSO_4$ (20 mM, pH 7.0) solution was added dropwise and allowed to react for another 20 min in dark at 37° C. Under radiation of UV-light (365 nm), a bright orange-red emission was clearly visible, indicating the successful formation of luminescent TMHA-liganded CuNCs. Finally, the resultant solution was stored in dark at 4° C. for use.

The optimal synthesis conditions, e.g., molar ratio of $Cu^{2+}$/TMHA, pH value, reaction temperature, and time were studied in detail respectively. To investigate the effect of $Cu^{2+}$ content in reaction system, 2 mL of $CuSO_4$ with varied concentrations was added into 10 mL of TMHA solution, in which the molar ratio of $Cu^{2+}$ to TMHA in this reaction system was from 5:1, 10:1, 15:1, 20:1, 30:1, 40:1, 60:1, 80:1, to 100:1. After reacted with gentle stirring in the dark at 37° C. and pH 7.0 for 20 min, the colloidal samples were obtained and tested by luminescence spectrophotometer. To better understand the influence of pH values on the formation of TMHA-liganded CuNCs, a series of experiments were carried out at different pH adjusting by 1.0 M NaOH or 1.0 M HCl under otherwise identical environments. Also, the effects of reaction temperature (20-70° C.), and reaction time (1-25 min) were studied respectively. The resultant samples were tested by luminescence spectrophotometer.

Figure 2:
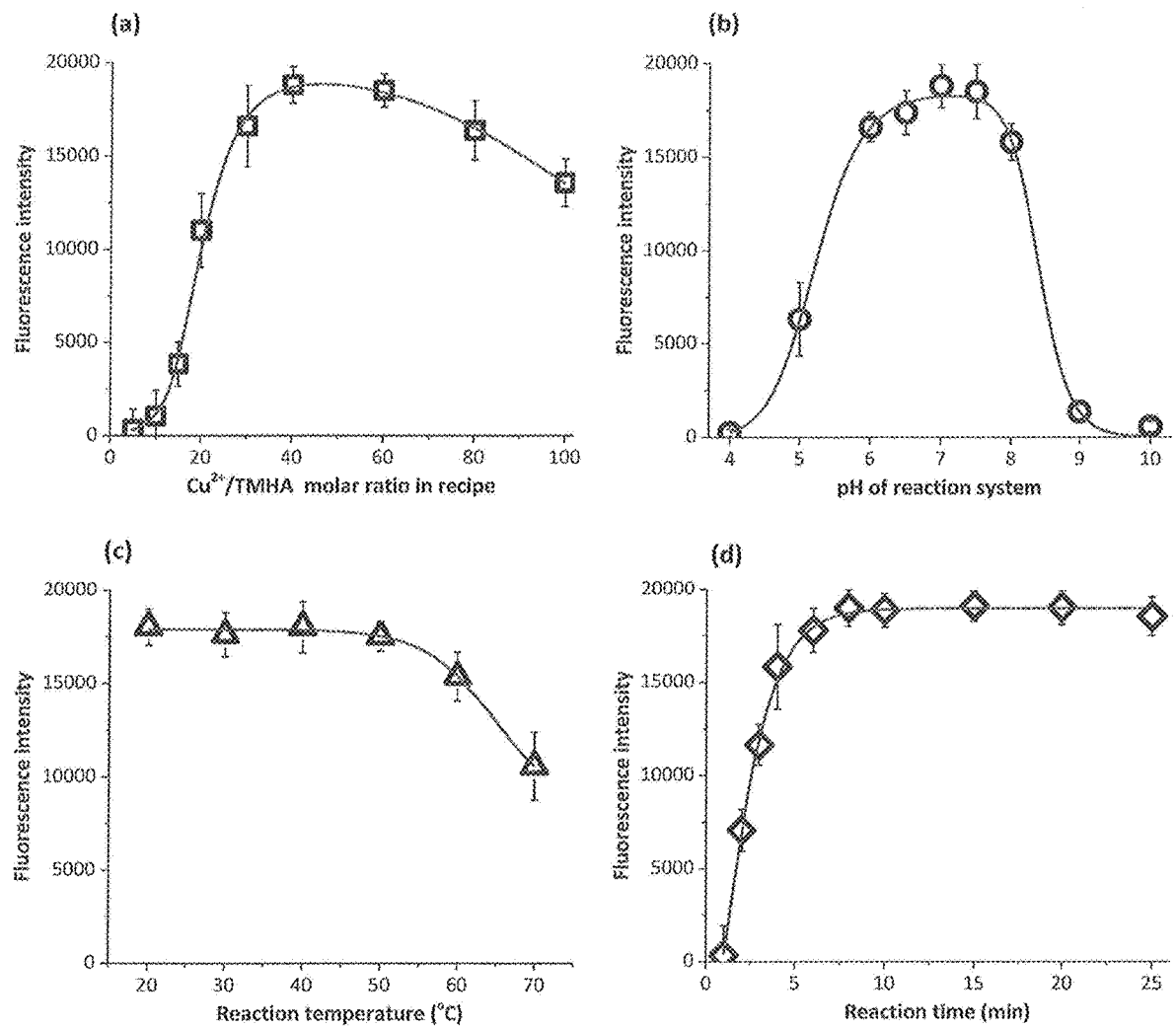
FIG. 2 provides graphs showing the effects of (a) molar ratios between $Cu^{2+}$ and TMHA, (b) reaction pH values, (c) reaction temperature, and (d) reaction time on the photoluminescence intensity of the resultant TMHA-liganded CuNCs.

Referring now to FIG. 2, there are provided graphs showing the effects of (a) molar ratios between $Cu^{2+}$ and TMHA, (b) reaction pH values, (c) reaction temperature, and (d) reaction time on the photoluminescence intensity of the resultant TMHA-liganded CuNCs. As shown in FIG. 2(a), the fluorescence intensity of TMHA-liganded CuNCs was enhanced with molar ratios between $Cu^{2+}$ and TMHA increasing from 5 to 40, and gradually declined with further increasing $Cu^{2+}$/TMHA ratio from 40 to 100. As shown in FIG. 2(b), the reaction pH values played an important role in the formation of high-quality TMHA-liganded CuNCs. The fluorescence intensity of the TMHA-liganded CuNCs greatly climbed up with the reaction pH values increasing from 4 to 7, and then began to decline rapidly. For instance, at reaction pH 10, the emission of TMHA-liganded CuNCs could be hardly monitored via the fluorescence spectroscopy. As shown in FIG. 2(c), the reaction temperature ranging from 20 to 50° C. was the ideal parameter in the formation of highly fluorescent TMHA-liganded CuNCs. As shown in FIG. 2(d), the fluorescence intensity of prepared TMHA-liganded CuNCs significantly improved as the synthetic time was prolonged from 1 min to 8 min. When the time was continually increased to 25 min, the fluorescence intensity of TMHA-liganded CuNCs kept constant. Based on all the observations, it was confirmed that the highest fluorescence intensity of the TMHA-liganded CuNCs can be obtained at the following optimized synthetic conditions: $Cu^{2+}$ and TMHA with the molar ratio of about 40 in a pH 7.0 solution, and then reacting at 37° C. for 4 h.

(3) Investigation of the Stability of TMHA-Liganded CuNCs

The evaluation of luminescent stability of TMHA-liganded CuNCs was conducted according to the following procedures. First, various concentrations of NaCl solution (100 μL) were mixed with TMHA-liganded CuNCs solution (900 μL) and incubated at 25° C. for 30 min. Second, 500 μL solution of TMHA-liganded CuNCs and various positive or negative ion solutions (500 μL, 2 mM) were mixed thoroughly and incubated at 25° C. for 30 min. Third, NaOH (1.0 M) or HCl (1.0 M) was introduced into 5 mL of TMHA-liganded CuNCs solution to adjust the system pH and incubated at 25° C. for 30 min. Finally, fluorescent spectra of TMHA-liganded CuNCs were measured at an excitation wavelength at 385 nm and emission wavelength at 610 nm.

Figure 3:
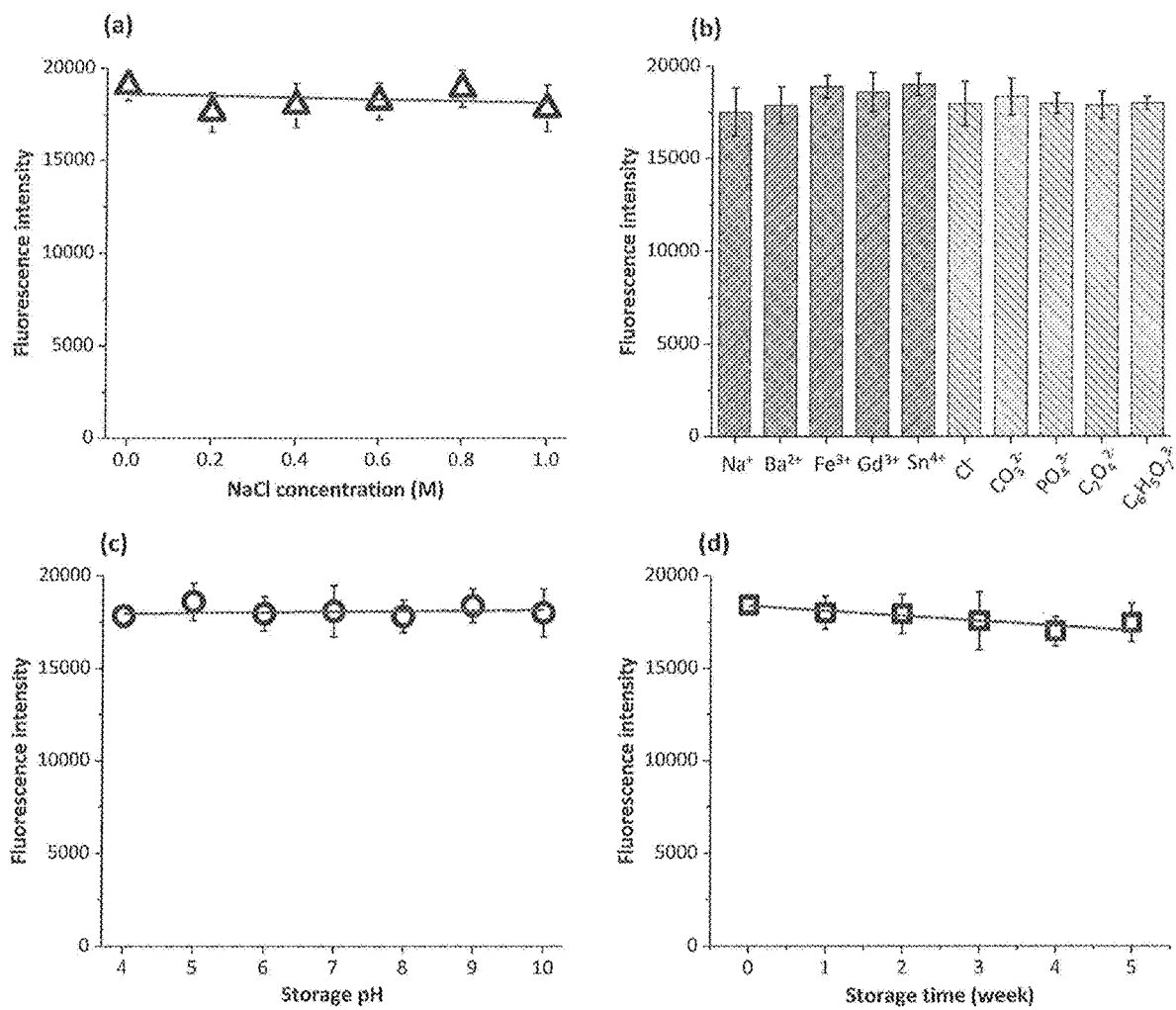
FIG. 3 provides graphs showing the effects of (a) NaCl concentrations (0-1 M), (b) common cations and anions, (c) pH values (4-10), and (d) storage time (0-5 weeks) on the fluorescence intensity of as-obtained TMHA-liganded CuNCs.

Referring now to FIG. 3, there are provided graphs showing the effects of (a) NaCl concentrations (0-1 M), (b) common cations and anions, (c) pH values (4-10), and (d) storage time (0-5 weeks) on the fluorescence intensity of as-obtained TMHA-liganded CuNCs. As shown in FIG. 3(a), the fluorescence intensity of TMHA-liganded CuNCs remained unchanged in the presence of NaCl solution with different concentrations (0, 0.2, 0.4, 0.6, 0.8 and 1.0 M), demonstrating a good stability of TMHA-liganded CuNCs in a strong ionic strength environment. More importantly, upon addition of 2 mM of other traditional metal ions, such as $Na^+$, $Ba^{2+}$, $Fe^{3+}$, $Gd^{3+}$, $Sn^{4+}$ and anions, such as $Cl^-$, $CO_3^{2-}$, $PO_4^{3-}$, $C_2O_4^{2-}$, $C_6H_5O_7^{3-}$, to the solution of TMHA-liganded CuNCs, it was found that all these selected ions manifested negligible interferences on the fluorescence intensity (FIG. 3(b)). A similar stable fluorescence performance was also recorded displayed in FIG. 3(c). Adjusting the pH values from 4.0 to 10.0 did not evidentially influence the corresponding fluorescence spectra of TMHA-liganded CuNCs. It obviously demonstrated that the TMHA-liganded CuNCs were insensitive to the pH values in the present buffer system. Moreover, after storage for 5 weeks in air at room temperature (25° C.), no precipitates, flocculation, or decline of fluorescence intensity was observed for TMHA-liganded CuNCs (FIG. 3(d)). All these results together suggested the outstanding stability of TMHA-liganded CuNCs, making them very promising for practical applications.

(4) The Effect of the Degree of Substitution (DS) of Thymine in TMHA on the Synthesis of TMHA-Liganded CuNCs Hyaluronic acid (HA) and thymine are two natural biomolecules; thymine responsible for efficiently chelating $Cu^{2+}$, and hydroxyl group of HA as the reducing agent for nucleation and growth of metal nanoclusters. The inventors of the present invention discovered that the degree of substitution (DS) of thymine was a key regulatory factor in the synthesis of TMHA-liganded CuNCs. $Cu^{2+}$ and TMHA with the molar ratio of about 50 in a pH 7.0 solution, and then reacting at 37° C. for 4 h.

Figure 4:
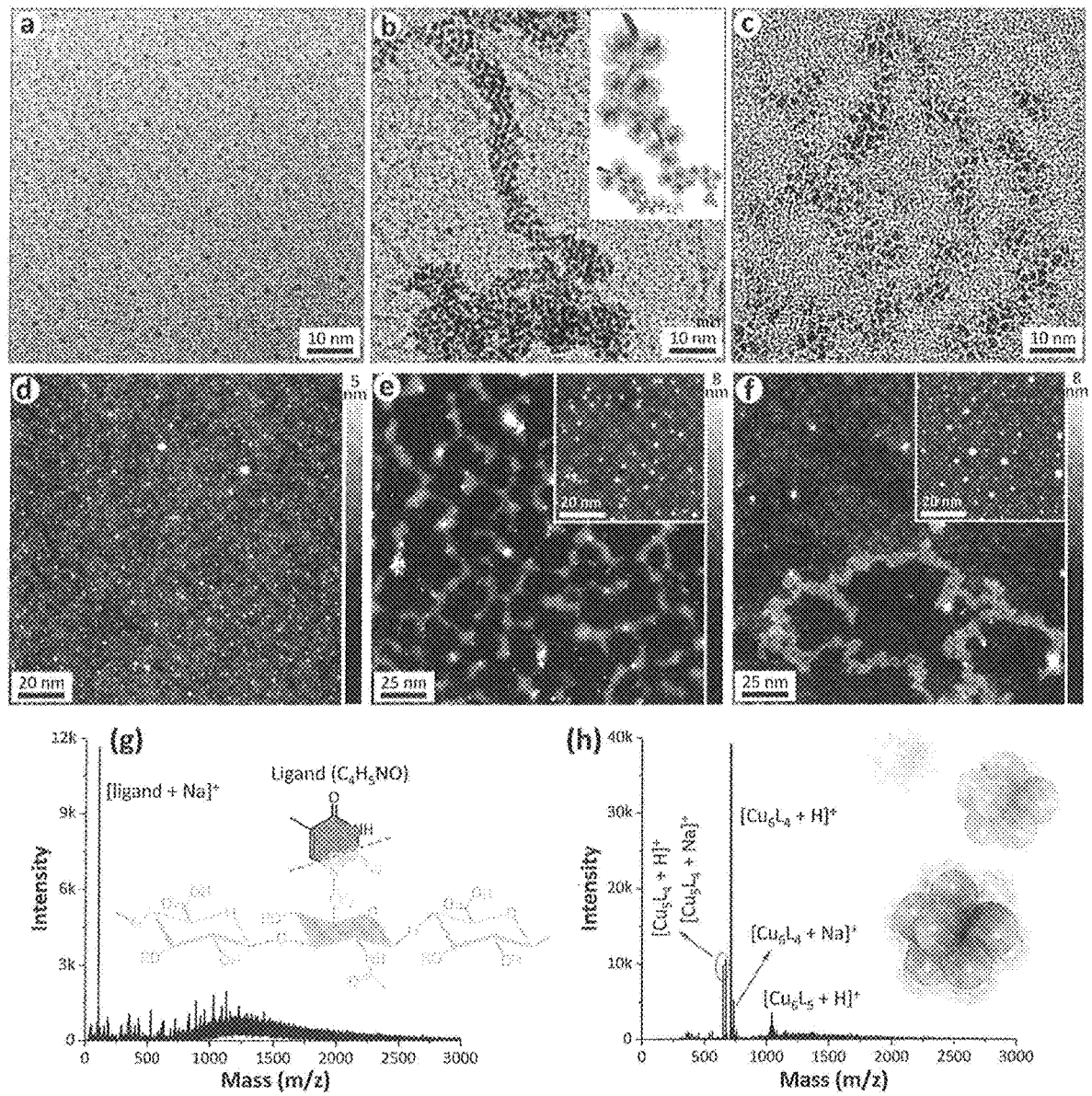
FIG. 4 provides photographs and graphs showing TMHA-liganded CuNCs prepared with TMHAs with different degree of substitutions (DS) of thymine.
Figure 4:
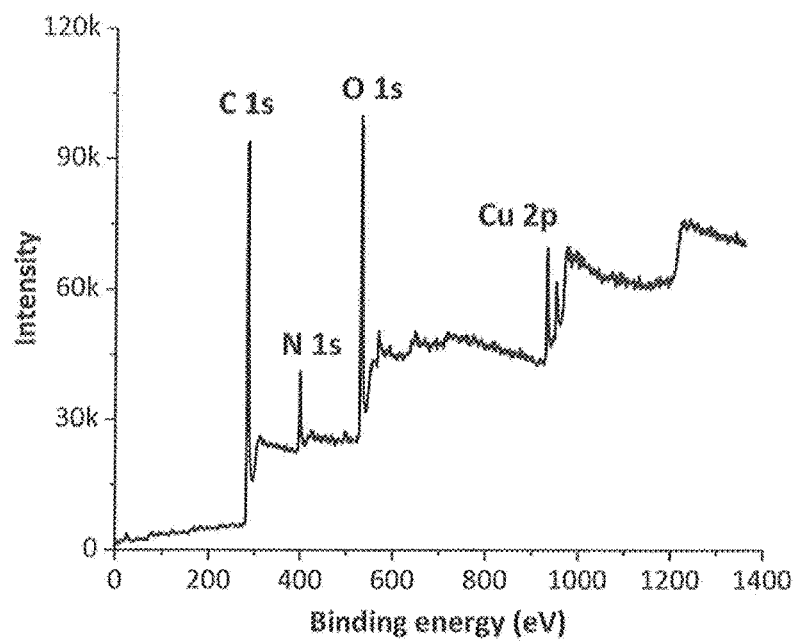
Figure 4:
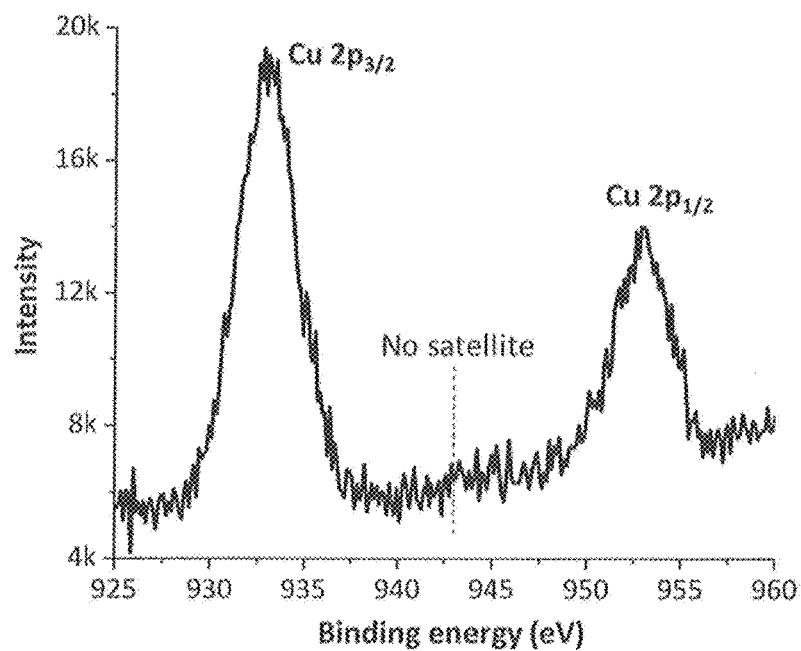

Referring now to FIG. 4, there are provided photographs and graphs showing TMHA-liganded CuNCs prepared with TMHAs with different degree of substitutions (DS) of thymine. FIGS. 4(a) and (d) show the TEM or AFM images of TMHA-liganded CuNCs prepared by TMHA with 3.2% DS of thymine respectively; FIGS. 4(b) and (e) show the TEM or AFM images of TMHA-liganded CuNCs prepared by TMHA with 10.5% DS of thymine respectively; FIGS. 4(c) and (f) show the TEM or AFM images of TMHA-liganded CuNCs prepared by TMHA with 20.1% DS of thymine respectively; FIGS. 4(g) and (h) show the MS spectra of TMHA or TMHA-liganded CuNCs respectively; and FIGS. 4 (i) and (j) show XPS spectra of (i) full region of CuNCs and (j) Cu 2p region. In FIG. 4, insets: (b, g, h) schematic illustration of TMHA-liganded CuNCs nanowires, ionization fragments and TMHA-liganded CuNCs, respectively; (e, f) isolated CuNCs that are composed of nanowires.

The DS of thymine at the level of 10.5% generated well-dispersed spherical CuNCs with diameters in a range of 0.5~3 nm, the average diameters of which are 1.64±0.48 nm. In contrast, at either a low (3.2%) or high (20.1%) level, abundant fluffy CuNCs were present with diameters of 1.08±0.72 nm and 1.96±0.83 nm, respectively. Subsequently replacing TMHA with blank HA under otherwise identical experiment factors only showed severely fused macromolecular networks (FIGS. 4 (i) and (j)). More surprisingly, the DS of 10.5% yielded one-dimensional assembly of TMHA-liganded CuNCs nanowire with diameters of 8.05±0.43 nm (FIGS. 4(b) and (e)). As the DS of theymine was increased to 20.1%, the nanowires were partly blurred in terms of seriously decayed length/diameter ratios (FIGS. 4(c) and (f)). A fine-tuning covalent bond between CuNCs and linear TMHA templates guaranteed that the CuNCs are self-assembled into highly ordered arrays, i.e. TMHA-liganded CuNCs. We highlighted that such nanowires efficiently improved TMHA-liganded CuNCs' fluorescence stability and intensity (seen below) based on aggregation induced emission (AIE).

(5) Replacement of Thymine with Other Ligands

Figure 5:
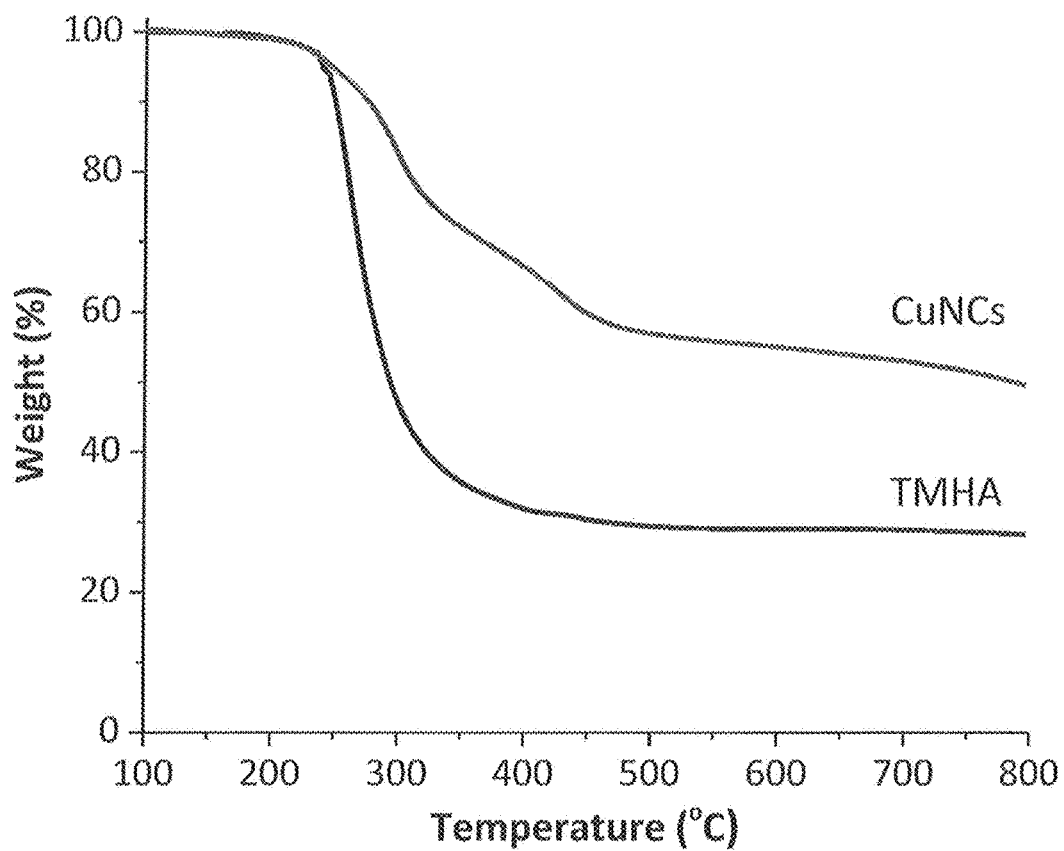
FIG. 5 is a graph showing thermogravimetric analysis of CuNCs with GSH ligand.

To more clearly detect individual CuNCs that form the nanowire, without varying core size of metal, the thymine ligand was replaced with thiolate by creating stronger Cu—S bonds. While GSH as a ligand formed CuNCs as expected, its use facilely disintegrates parent nanowire into its building units, i.e. CuNCs. As shown in FIG. 5, there is a graph showing thermogravimetric analysis of CuNCs with GSH ligand. Here, the strategy of ligand exchange was employed to disintegrate parent nanowire into its building blocks, for example CuNCs. The as-prepared TMHA-templated CuNCs (1 mL) was added to GSH aqueous solution (0.05 M, 5 mL) and kept for stirring for 8 h at room temperature. A white precipitation will be produced as the reaction processed. The resulting supernate was collected by centrifugation at 8000 rpm for about 10 min. The GSH-stabilized CuNCs were precipitated from the supernate by addition of ethanol and washed with ethanol repeatedly for three times. Finally, the product was freeze-dried and stored in the refrigerator for long-term preservation.

(6) Characterization of TMHA-Liganded CuNCs

Figure 6:
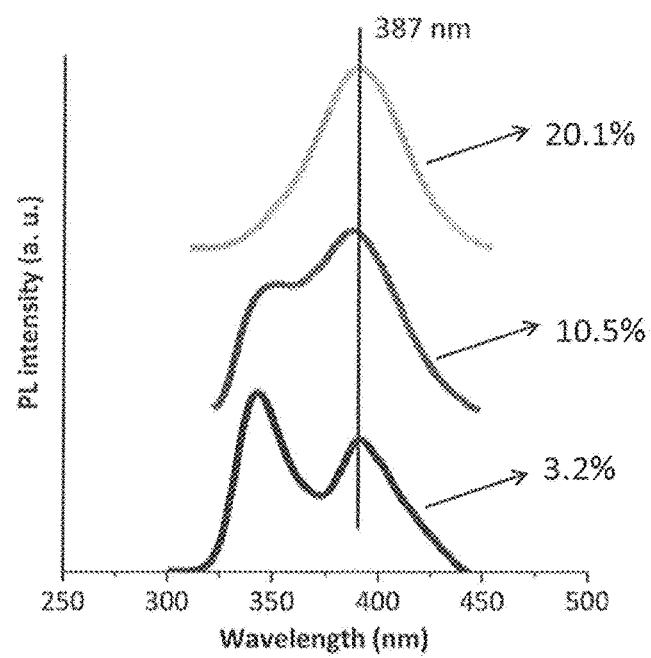
FIG. 6 is a graph showing excitation (measured at $\lambda_{em}$=613 nm) spectra of CuNCs obtained using the DS of thymine at 3.2%, 10.5%, and 20.1, respectively.

Of note, the intermediate DS at 10.5% led to intact, spherical, and uniform CuNCs, corroborating via section profile analysis and polydispersity index. Upon careful calculation from HR-TEM image, inter-fringe spacing of 0.207 nm was found, which matched well with (111) crystal plane of face-centered metallic Cu. FIG. 6 is a graph showing excitation (measured at $\lambda_{em}$=613 nm) spectra of CuNCs obtained using the DS of thymine at 3.2% (blue), 10.5% (red), and 20.1 (green), respectively.

In the following sections, TMHA-liganded CuNCs prepared by TMHA at DS of 10.5% was deliberately used unless otherwise noted.

As a supplement to electron microscope, mass spectrometry (MS) has also been proved to be a reliable tool in cluster size analysis. Here we attempted to utilize high-resolution electrospray ionization MS (ESI-MS) to identify the precise molecular formula of subnanometer-sized CuNCs. Notably, the pure HA gave no any visible ion signals, mainly due to its low ionization efficiency in positive ion mode. The positive ionization of TMHA, in contrast, produced a single peak at m/z=106.1936 (FIG. 4(g)). It can be ascribed to a formula of $[C_4H_5NO+Na]^+$ owing to the loss of HNCO from thymine. $C_4H_5NO$ instead of THMA acting as a ligand in ionization of CuNCs contributed to release abundant ion signals after screening several measurement parameters. Those parameters delivering the appropriate energy to facilitate the decomposition of thymine and, thus chosen as optimal, were capillary voltage of ca. 4500 V and dry temperature of 150° C. By combining element analysis and the highest ion peak at m/z=1043.2545 (FIG. 4(h)), the definitive formula of CuNCs was determined as $Cu_6L_5$. Other ion peaks in a low mass range also corresponded precisely with fragments of $Cu_6$-involved species. As a result, the $Cu_6$ clusters were the dominant species, suggesting superior monodispersity of CuNCs synthesized by TMHA with DS of thymine at 10.5% relative to two controls with the DS at 3.2% and 20.1%.

X-ray photoelectron spectroscopy (XPS) analysis revealed that CuNCs were made up of all the anticipated elements, including C, O, N, and Cu. The inorganic content in CuNCs was calculated to be 29.8 wt %. Moreover, two intense signals at 932.3 and 952.1 eV were assigned to binding energies of $2p_{3/2}$ and $2p_{1/2}$ electrons of $Cu^0$, and no satellite signals implied the lack of $Cu^{2+}$. It was worthwhile mentioning that $2p_{3/2}$ binding energy of $Cu^0$ was very close to that of $Cu^+$. Therefore, the valence states of as prepared CuNCs most likely lied between 0 and +1.

Figure 7:
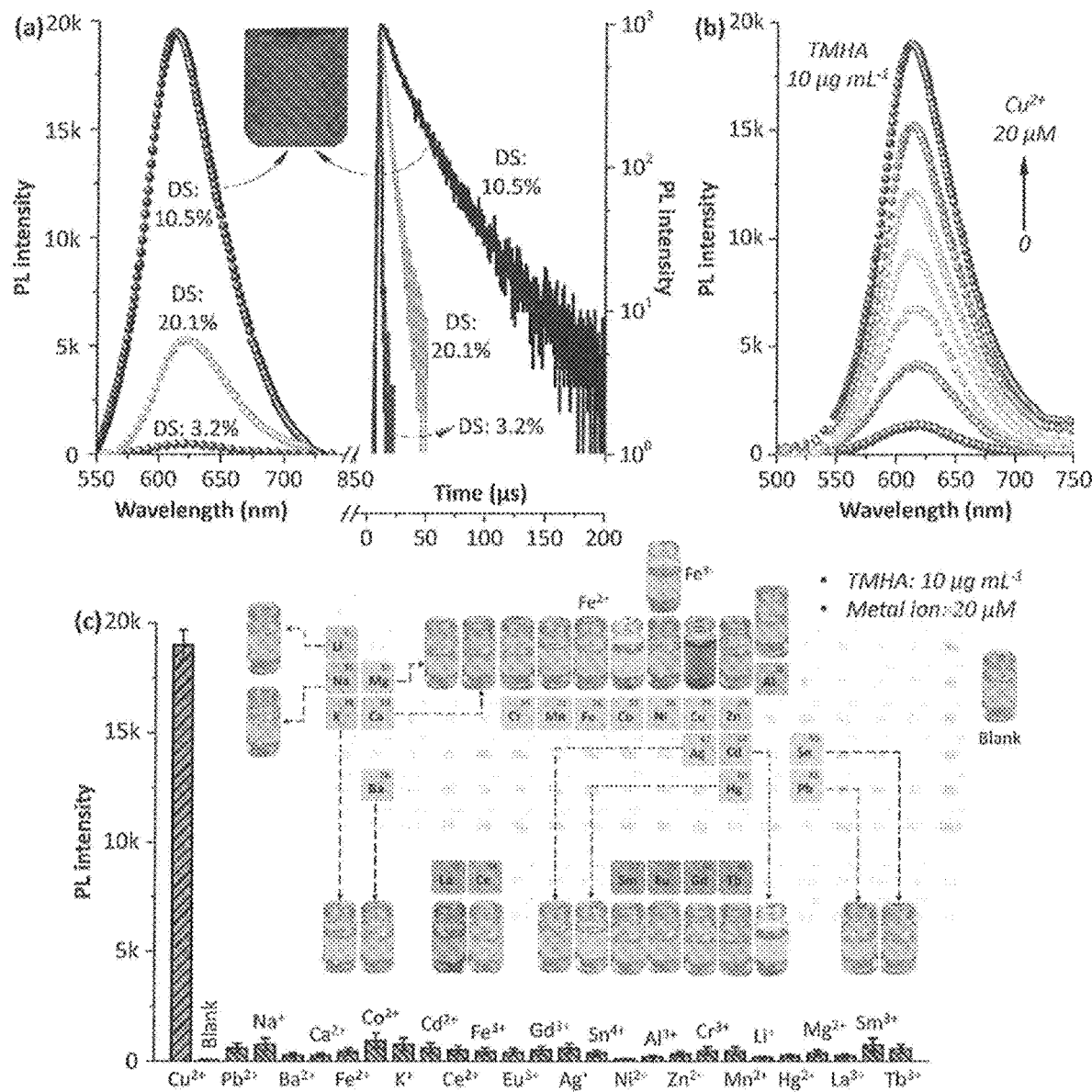
FIG. 7 provides graphs showing: (a) PL spectra (Left) and decay profiles (right) with different DS of theymine. Inset: image with 365 nm excitation. (b) PL response of TMHA probe versus $Cu^{2+}$ content. (c) PL and color change (inset) of TMHA probe for $Cu^{2+}$ against various metals.

Referring now to FIG. 7, there are provided graphs showing: (a) PL spectra (Left) and decay profiles (right) with different DS of thymine. Inset: image with 365 nm excitation. (b) PL response of TMHA probe versus $Cu^{2+}$ content. (c) PL and color change (inset) of TMHA probe for $Cu^{2+}$ against various metals.

(7) TMHA as a Probe for Detection of $Cu^{2+}$ Ions

Five urine samples, in which three of them were collected from healthy adult volunteers and the rest collected from adult volunteers with PD, were diluted by acetonitrile for removing the interference of protein and other biospecies in urine, respectively. After centrifugation with a speed of 12,000 rpm for 10 min at 10° C., the supernatant solution was collected for the following experiments. First, the supernatant was diluted by deionized water in order to decrease the $Cu^{2+}$ concentrations remaining in the supernatant. Then, 100 μL urine sample was mixed with 200 μL of TMHA (0-40 μg mL$^1$), and incubated for 10 min at 25° C. before it was examined by fluorescence spectrometer.

It is worthy to note that, optical feature was clearly different from the surface plasmon resonance of large Cu nanoparticle at 560 nm. The broadening of XRD peaks into a baseline was consistent with tiny size of CuNCs. Interestingly, the subnanoscaled CuNCs possessed DS-dependent photoluminescence (PL) features. Under excitation of 385 nm, 10.5% DS-induced nanowires gave a bright and stable red emission peaked at 613 nm, a long lifetime of 57 μs, and large quantum yield of 14.8% (FIG. 7(a)). These properties faded rapidly for those of less ordered CuNCs assemblies, hinting the self-assembly driven AIE. The more CuNCs packing tightly and orderly, the more stable and intense PL responses. By tuning reaction factors, our clean synthesis route relied on TMHA (chelating, reducing $Cu^{2+}$ and templating self-assembly into CuNC nanowire), eliminating impurities that traditional routes introduced, and affording striking PL properties. For example, the PL intensity of TMHA sensor was linearly and clearly improved in response to $Cu^{2+}$ concentrations (FIG. 7(b)), corresponding to an extremely low detection limit of 2.2 ppb. Compared with currently reported methods, this analytical performance showed about 1.5 and 480 times smaller than state-of-the-art probes and maximal levels of drinking water set by U.S. EPA, respectively. Also, the optical property was selective toward $Cu^{2+}$ relative to foreign ions in FIG. 7(c). Taken together, TMHA can be used as colorimetric and fluorometric $Cu^{2+}$ probe with high sensitivity and selectivity.

(8) Antioxidant Function of CuNCs

The capability of CuNCs to functionally mimic cellular antioxidant enzymes was studied. Strikingly, CuNCs could violently decompose $H_2O_2$ based on a first-order reaction kinetics (FIG. 8(a)). We then studied the GPx-like activity of CuNCs via the nitroblue tetrazolium (NBT) assay. The initial rates recorded at various assay conditions were displayed in FIG. 8(b), which directly supported the GPx-like function of CuNCs. In addition, CuNCs had a remarkable SOD-like activity and the production of mass $O_2$ from $KO_2$ as a superoxide source deduced the working principle:

disproportionation of superoxide to $H_2O_2$ and $O_2$ (FIG. 8(c)). Moreover, CuNCs had obvious multienzyme advantages over preexisting metals that are used as cellular antioxidants (FIG. 8(d)).

Figure 8:
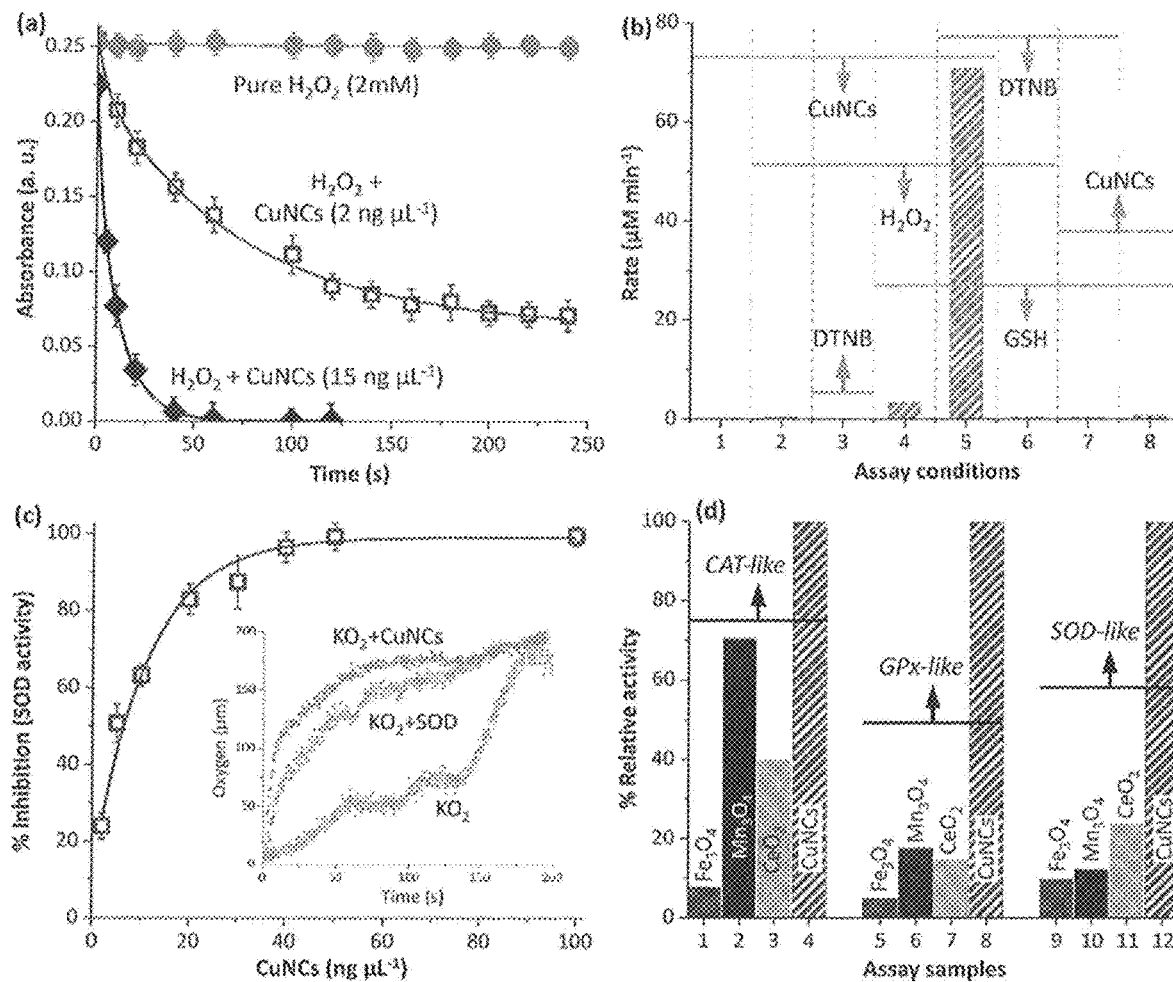
FIG. 8 provides graphs showing: (a) UV absorption of $H_2O_2$ reacting with CuNCs. (b) Initial rates of GPx-like activities of CuNCs and various controls. (c) SOD-like activities of CuNCs. Inset: $O_2$ generation rate. (d) Comparison of catalytic activity of CuNCs with other metals.

Referring now to FIG. 8, there are provided graphs showing: (a) UV absorbance of $H_2O_2$ reacting with CuNCs; (b) Initial rates of GPx-like activities of CuNCs and various controls; (c) SOD-like activities of CuNCs (inset: $O_2$ generation rate); and (d) Comparison of catalytic activity of CuNCs with other metals.

(9) Non-Invasive Diagnostic of PD by TMHA $Cu^{2+}$ contents in human urine samples were measured using TMHA as probe. Remarkably, red fluorescence only appeared in the urine samples from PD patients. Considering its high specificity and simple operations, TMHA may open new opportunities in early diagnosis and risk assessment for PD.

Figure 9:
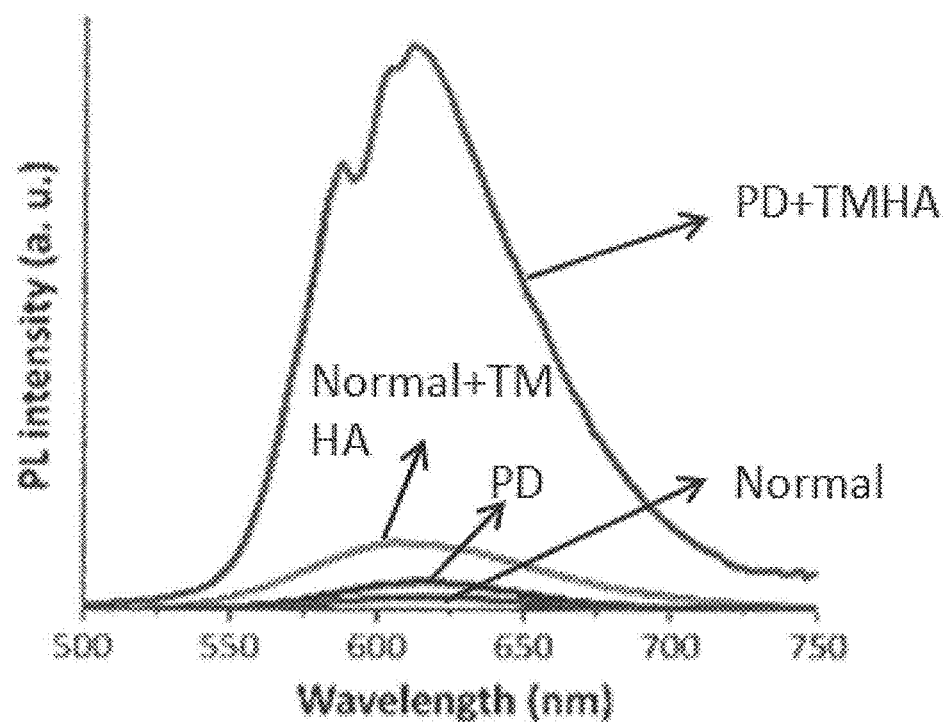
FIG. 9 provides graphs showing detection of urine $Cu^{2+}$ for early diagnosis of PD.

Referring now to FIG. 9, there is provided graphs showing detection of urine $Cu^{2+}$ for early diagnosis of PD.

(10) In Vitro Cell Experiments

PC12 (a rat adrenal medulla pheochromocytoma cell line), SHSY-5Y (a human neuroblastoma cell line), and HEK293 (a human embryonic kidney cell line) cells were cultured in Dulbecco's modified eagle medium (DMEM) medium supplemented with 10% (v/v) fetal bovine serum, 2 mM L-glutamine, 100 U $mL^{-1}$ penicillin, 100 µg $mL^{-1}$ streptomycin at 37° C. and 5% $CO_2$.

Methyl thiazolyl tetrazolium (MTT) assay was performed to measure in vitro cytotoxicity of TMHA by measuring cell viability. For the MTT assay, SHSY-5Y cells were seeded in 96-well plates at a density of 5000 viable cells per well and incubated for 24 h at 37° C. and 5% $CO_2$ to allow cell attachment. Then, the cells were incubated with blank TMHA solution (no $Cu^{2+}$ addition) at indicated concentrations. The cells were subsequently incubated for 24 h at 37° C. and 5% $CO_2$. After that the medium was replaced with fresh DMEM containing 5 mg $mL^{-1}$ MTT, the cells were incubated for an additional 4 h. After the removal of the MTT solution, the purple formazan crystals were dissolved with DMSO, and the absorbance was monitored at 570 nm on a micro-plate reader (FL600, Bio-Tek). The results were expressed as the mean values of three measurements. The same processes were performed to measure the in vitro cytotoxicity of pure THMA against HEK 293 cells and PC12 cells. TMHA was nontoxic at dosage high as 500 µg $mL^{-1}$.

We then investigated the cytoprotective property of TMHA in experimental cell model of PD phenotype. The model was generated via treating the rat adrenal pheochromocytoma cell (PC12) with $MPP^+$ (1-methyl-4-phenylpyridinium), an active metabolite of MPTP (1-methyl-4-phenyl-1,2,3,6-tetrahydropyridine).

1-methyl-4-phenyl-1,2,3,6-tetrahydropyridine (MPTP) is a neurotoxin. It is not toxic per se, but after it enters the brain, this neurotoxin is metabolized into the compound 1-methyl-4-phenylpyridine ($MPP^+$). $MPP^+$ can destroy DA-ergic neurons in the substantia nigra. At the same time, $MPP^+$ can interfere with NADH dehydrogenase, an important substance in the respiratory chain of mitochondrial metabolism, thus causes cell death and accumulation of free radicals. The mass death of DA-ergic neurons caused by this process severely affects motion control by the cerebral cortex, resulting in similar symptoms of PD. Therefore, MPTP and $MPP^+$ are widely used in the establishment of PD-related animal and cell models as well as the research and development of PD medications.

Figure 10:
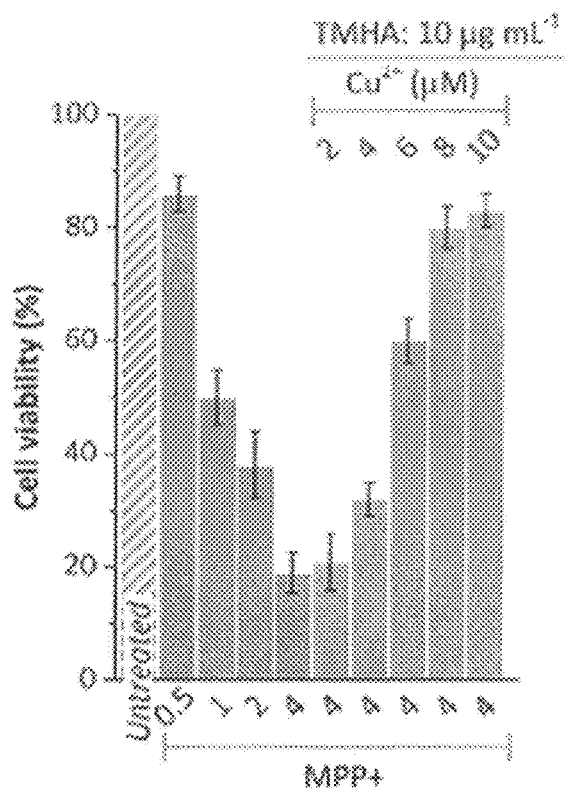
FIG. 10(a) provides bar graphs showing the data of cell viability (***p<0.001)
FIG. 10(b) shows dead (red) cells stained by PI dye, where the cells were treated with 4 mM $MPP^+$, 2 μM $Cu^{2+}$ and 10 μg ml$^{-1}$ TMHA.
FIG. 10(c) shows viable (green) cells stained by calcein-AM, where the cells were treated with 4 mM $MPP^+$, 10 μM $Cu^{2+}$ and 10 μg ml$^{-1}$ TMHA.
Figure 10:
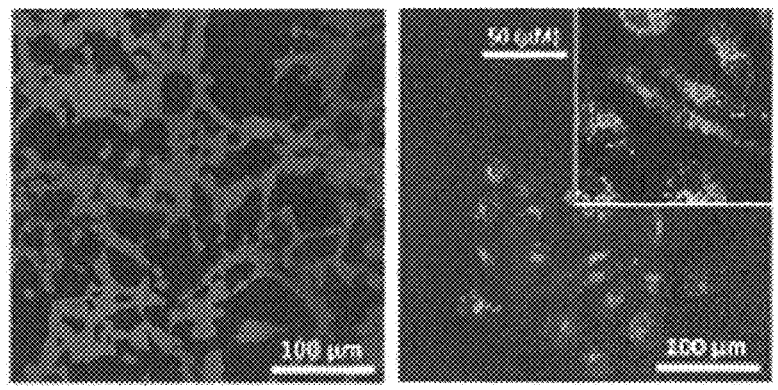

PC12 cells were cultured in 6-well plates in the absence or presence of $Cu^{2+}$ and THMA. Various concentrations of $MPP^+$ (0.5-4 mM) was then added. The relative viability of cells was also determined by MTT assays. 4 mM $MPP^+$ triggered severe cytotoxicity of PC12 cells (i.e. only less than 20% cell viability). Excitingly, 4 mM $MPP^+$ triggered cytotoxicity was fully reversed by 8 µM $Cu^{2+}$ and 10 µg $ml^{-1}$ TMHA (i.e. more than 80% cell viability). The data of cell viability are shown in FIG. 10(a) (***p<0.001).

The cellular morphological alterations were acquired using confocal laser scanning microscopy (CLSM). For the observation of viable and dead cells on CLSM, 3',6'-Di(O-acetyl)-4',5'-bis[N,N-bis(carboxymethyl)aminomethyl]fluorescein (i.e. tetraacetoxymethyl ester (calcein-AM)) was applied to stain the viable cells as green fluorescence ($\lambda_{ex}$=490 nm, $\lambda_{em}$=515 nm) and propidium iodide (PI) was employed to stain dead cells as red fluorescence ($\lambda_{ex}$=535 nm, $\lambda_{em}$=617 nm). Specifically, 0.1 mL of calcein-AM solution (20 mM) and 0.1 mL of PI solution (20 mM) were both added after the removal of culture medium. After 10 min of incubation, the two staining solutions were quickly removed, and the cells were rinsed by PBS twice. The obtained cells could be subsequently visualized by CLSM. FIG. 10(b) shows the dead (red) cells stained by PI dye, where the cells were treated with 4 mM $MPP^+$, 2 µM $Cu^{2+}$ and 10 µg $ml^{-1}$ TMHA; FIG. 10(c) shows viable (green) cells stained by calcein-AM, where the cells were treated with 4 mM $MPP^+$, 10 µM $Cu^{2+}$ and 10 µg $ml^{-1}$ TMHA.

In order to directly observe reactive oxygen species (ROS) using CLSM, PC12 cells were first seeded in a CLSM-exclusive culture disk and allowed to adhere overnight at 37° C. under 5% $CO_2$ gas. After incubation with 1 mL of 2',7'-dichlorofluorescein diacetate (DCFH-DA) for about 20 min, the culture solutions were replaced by fresh media (pH=7.4) containing the following substances: (a) 4 mM of $MPP^+$ as control, (b) 4 mM of $MPP^+$, 10 of µg $mL^{-1}$ TMHA, (c) 4 mM of $MPP^+$, 10 µM of $Cu^{2+}$, (d) 4 mM of $MPP^+$, 10 µg $mL^{-1}$ of TMHA, 2 µM of $Cu^{2+}$, (e) 4 mM of $MPP^+$, 10 µg $mL^{-1}$ of TMHA, 4 µM of $Cu^{2+}$; (f) 4 mM of $MPP^+$, 10 µg $mL^{-1}$ of TMHA, 6 µM of $Cu^{2+}$, (g) 4 mM of $MPP^+$, 10 µg $mL^{-1}$ of TMHA, 8 µM of $Cu^{2+}$, and (h) 4 mM of $MPP^+$, µg $mL^{-1}$ of TMHA, 10 µM of $Cu^{2+}$, respectively. The cells were washed by fresh PBS twice after another incubation at 37° C. in 5% $CO_2$ for 30 min. The levels of intracellular ROS were evaluated by detecting the fluorescence of newly formed DCF ($\lambda_{ex}$=488 nm, $\lambda_{em}$=525 nm). The data of intracellular ROS levels are shown in FIG. 11(a); ***p<0.001.

Figure 11:
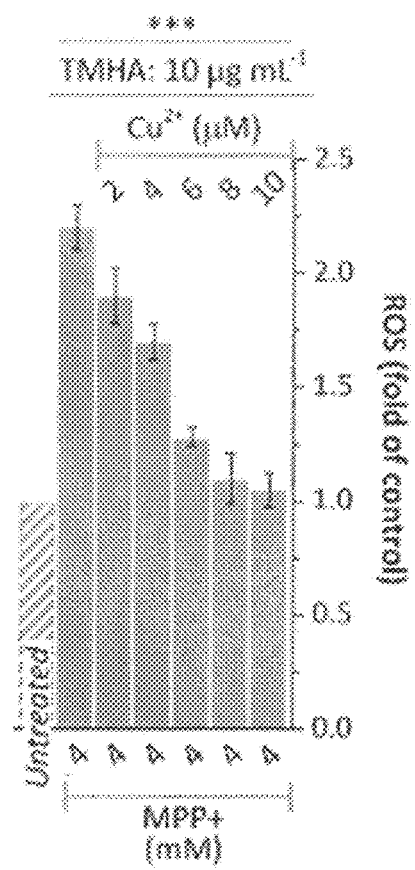
FIG. 11(a) provides bar graphs showing the data of the intracellular ROS levels, ***p<0.001.
FIG. 11(b) shows a CLSM image of intracellular ROS in the cells that were treated with 4 mM of $MPP^+$, 10 of μg mL$^{-1}$ TMHA, and stained using a specific fluorescence probe DCFH-DA.
FIG. 11(c) shows a CLSM image of intracellular ROS in the cells that were treated with 4 mM of $MPP^+$, 10 of μg mL$^{-1}$ TMHA, 10 μM of $Cu^{2+}$, and stained with DCFH-DA.
Figure 11:
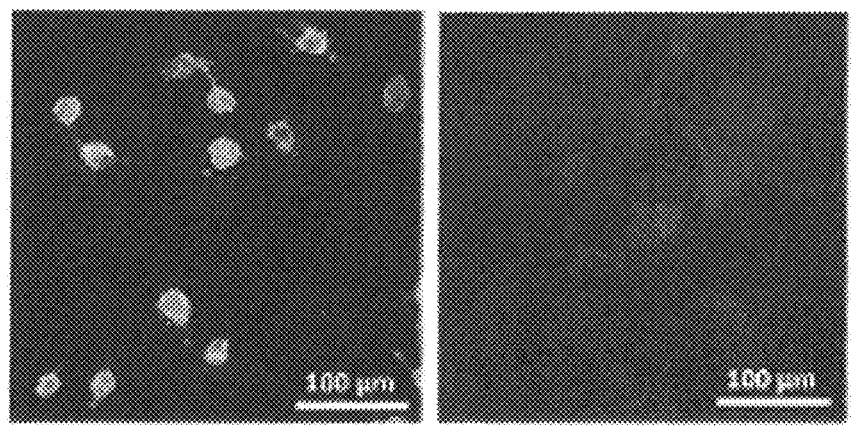

FIG. 11(b) shows a CLSM image of intracellular ROS in the cells that were treated with 4 mM of $MPP^+$, 10 of µg $mL^{-1}$ TMHA, and stained by specific fluorescence probe DCFH-DA; FIG. 11(c) shows a CLSM image of intracellular ROS in the cells that were treated with 4 mM of $MPP^+$, 10 of µg $mL^{-1}$ TMHA, 10 µM of $Cu^{2+}$, and stained by specific fluorescence probe DCFH-DA. Obvious decline of ROS-specific fluorescent intensity demonstrated that TMHA was capable of scavenging intracellular elevated ROS efficiently. The characteristic 1:2:2:1 hydroxyl radical spin further demonstrated the reduction of intracellular ROS induced by TMHA treatment.

(11) In Vivo Protection Experiments

Generally, it is widely accepted that administrations of 1-methyl-4-phenyl-1,2,3,6-tetrahydropyridine (MPTP) can result in clinical symptoms of animals remarkably similar to sporadic PD in humans. Hence, for our experiments, we utilized MPTP to produce parkinsonian symptoms in animal models of PD. Briefly, the C57BL/6 mice were randomly divided into 7 groups (n=5 mice/group), i.e., blank Control (normal saline), high dose of TMHA (100 mg $kg^{-1}$), low dose of TMHA (50 mg kg$^{-1}$), high dose of MPTP (30 mg kg$^{-1}$), low dose of MPTP (10 mg kg$^{-1}$), MPTP+TMHA (30 mg kg$^{-1}$+10 mg kg$^{-1}$), and MPTP+TMHA (30 mg kg$^{-1}$+20 mg kg$^{-1}$). Specifically, for the model group, MPTP was given by continuous intraperitoneal injection for at least 4 days to generate the mouse model of PD. The blank control group and THMA group were treated with saline and THMA by ip injection, respectively. For the MPTP+TMHA groups, the TMHA (dosage: 10 or 20 mg kg$^{-1}$) was injected intraperitoneally 0.5 h in advance (once per day) and then MPTP of 30 mg kg$^{-1}$ was injected intraperitoneally for 7 days.

Figure 12:
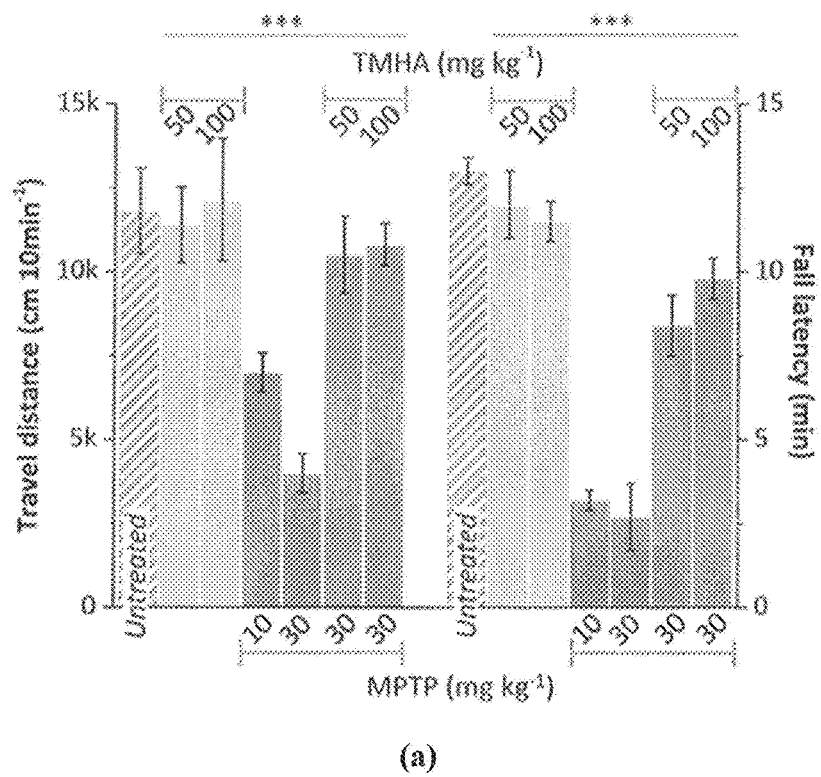
FIG. 12(a) shows the traveled distance and fall latency of mice with memory deficit, ***p<0.001.
FIG. 12(b) shows a mitochondrion from an animal treated with high dose of MPTP (30 mg kg$^{-1}$), where as outlined via red line, the mitochondrion shows swollen, vacuolar shapes and severe cristae disruption.
FIG. 12(c) shows a mitochondrion from an animal treated with MPTP (30 mg kg$^{-1}$)+TMHA (30 mg kg$^{-1}$), where as outlined via red line, the mitochondrion displays a normal morphology.
Figure 12:
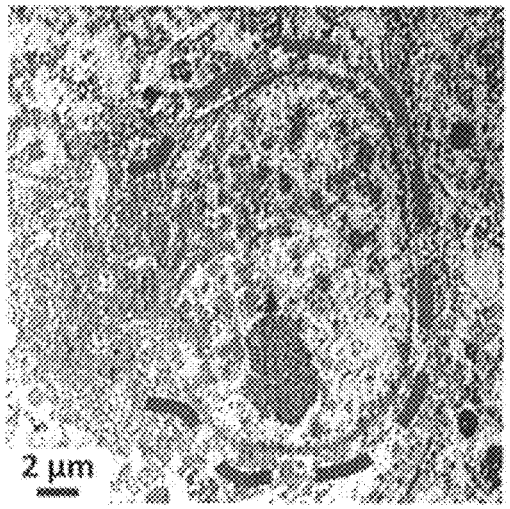
Figure 12:
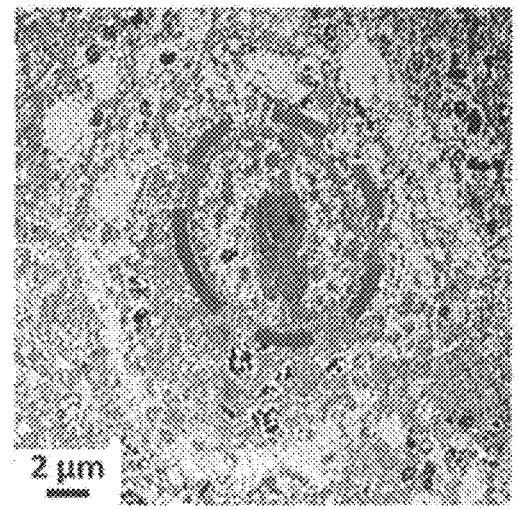

The motor function was assessed via swim test. Each animal was placed in a circular pool with dimension of diameter 120 cm and height 80 cm. The depth of water (25° C.) was 60 cm. The traveled distance (cm 10 min$^{-1}$) and duration (sec) were both recorded at 10-min interval using a tracking system (Shanghai Jiliang Software Technology Co., Ltd.). The motor coordination and balance were measured using a rotarod (Ugo Basile). Mice were given three trials of 15 min on rotating rod that started at 10 rpm and accelerated to 22 rpm over 30 s. The inter-trial interval was 3 min. The time of falling from the rod was measured and averaged for each group. FIG. 12(a) shows the traveled distance and fall latency of mice with memory deficit; ***$p<0.001$. These data demonstrated that TMHA treatment could restore the cognitive activities of MPTP-treated animals.

Variation in mitochondria morphology is an early and important sign of ROS-induced mitochondrial dysfunction. Here, we used TEM to visualize mitochondrial morphology alterations. Generally, brain tissues from C75BL/6 mice were sequentially fixed overnight in a mixture of cold 2.5% glutaraldehyde in 0.1 M PBS (pH 7.2) and 2% paraformaldehyde in 0.1 M phosphate buffer solution (pH 7.2) before being placed in epoxy resin. The embedded samples were loaded into capsules and polymerized at 38° C. for 9 h and then at 60° C. for 48 h. Thin sections were made using an ultramicrotome (RMC, USA) and collected on a copper grid. Appropriate areas for sections were cut at 100 nm thickness, and the sections were stained with saturated 4% uranyl acetate/4% lead citrate prior to TEM before examination with a transmission electron microscope (JEM-2100F) at 80 kV. FIG. 12(b) shows a mitochondrion from an animal treated with high dose of MPTP (30 mg kg$^{-1}$), where as outlined via red line, the mitochondrion shows swollen, vacuolar shapes and severe cristae disruption; in contrast, FIG. 12(c) shows a mitochondrion from an animal treated with MPTP (30 mg kg$^{-1}$)+TMHA (30 mg kg$^{-1}$), where as outlined via red line, the mitochondrion displays a normal morphology.

(12) α-Syn Aggregation Kinetics Experiments with Singular CuNCs with Different Ligands CuNCs modified with different ligands were prepared according to literatures. Thioflavin T (abbreviation: ThT) is a highly sensitive fluorescent marker used to identify the presence of amyloid. When ThT is incubated together with monomers of polypeptides or proteins, its fluorescence does not change substantially. When ThT encounters amyloid polypeptide or protein with a fiber structure, it will immediately adjacent to the amyloid polypeptides or proteins and its fluorescence intensity will increase exponentially. Therefore, ThT is widely used as a maker to monitor amyloidosis of peptides or proteins. This embodiment adopts ThT fluorescent labeling method to monitor the kinetics process of fibrosis aggregation of α-syn in the presence of CuNCs. The specific experiment method is as follows:

Pretreatment of α-syn monomers: Dissolve freeze-dried α-syn powder (Bachem Corp.) in HFIP to obtain a 1 g/L α-syn solution. Incubate it at room temperature for 2-4 h after sealing, then use high-purity nitrogen to blow HFIP dry at an appropriate flow rate in a fume cupboard, dissolve the dried α-syn in 200 μL of DMSO, seal the solution, keep it in a −20° C. refrigerator for future use, for at most one week. Before use, dilute the α-syn DMSO solution with profuse phosphate buffer solution (PBS, 10 mM, pH=7.4) to 20 M, to obtain a α-syn PBS solution. All the α-syn PBS solutions in the experiment are prepared just before use.

Sample preparation and detection: Add ligand modified CuNCs to α-syn PBS solution to reach final concentrations of 5 ppm and 35 μM for CuNCs and α-syn, respectively. Incubate the solution continuously in a 96-well plate at 37° C., monitor the fluorescence intensity by microplate reader every 10 minutes, and characterize the kinetics process of α-syn aggregation through the change of fluorescence intensity of ThT. The experimental group takes the ligand modified CuNCs. The ligand control group adopts ligand molecules not combined to CuNCs. The blank control group adopts α-syn only.

Figure 13:
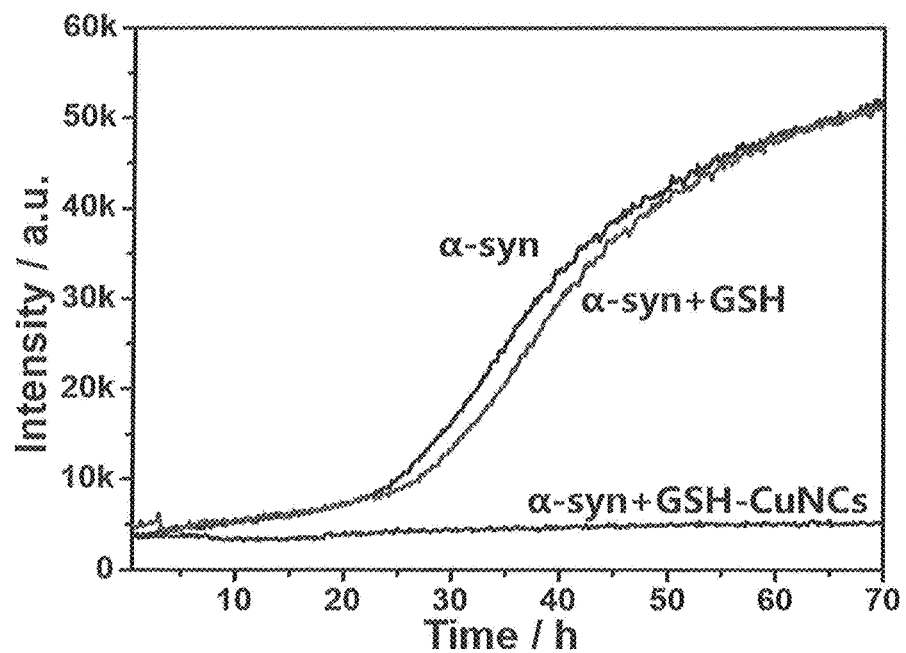
FIG. 13 provides graphs showing the effect of L-glutathione (GSH) modified CuNCs (GSH-CuNCs) on α-syn fibrosis kinetics.

Referring now to FIG. 13, there are provided graphs showing the effect of L-glutathione (GSH) modified CuNCs (GSH-CuNCs) on α-syn fibrosis kinetics. The results indicate that in the incubation process of 35 μM α-syn at 37° C., ThT-labeled fluorescence intensity increases rapidly from the 25$^{th}$ hour, demonstrating that α-syn aggregation and fibrosis happened. The result of the ligand control group indicates that using ligand GSH alone does not have an obvious effect on aggregation kinetics of α-syn. As for the experimental group with addition of CuNCs, ThT-labeled fluorescence intensity remains near the base line without any increase throughout the 70 hours of experiment, suggesting that GSH modified CuNCs can inhibit α-syn aggregation and fibrosis completely, and the effect is due to CuNCs, but not the GSH ligands.

In certain embodiments, CuNCs were modified with other ligands, e.g. including L(D)-cysteine, N-isobutyryl-L(D)-cysteine (L(D)-NIBC) and N-acetyl-L(D)-cysteine (L(D)-NAC), and the modified CuNCs are also studied using the same protocols. A similar phenomenon is also observed for CuNCs modified with different ligands, and the same conclusion can be made: these ligands per se cannot influence α-syn aggregation and fibrosis, while ligand-modified CuNCs can inhibit α-syn aggregation and fibrosis completely.

(13) MPP$^+$ Induced PD Cells (SH-sy5y) Model Experiment

The experiment uses cell viability obtained from the test result of CCK-8 method as an indicator, to reflect the resistance efficacy of ligand-modified CuNCs against the toxic effect of MPP$^+$ (a common-used neurotoxin) in SH-sy5y cell model of PD to demonstrate their neuroprotective effect on PD. Specific method:

1) Take SH-sy5y cells in the logarithmic growth phase. Dilute them with complete medium to form a cell suspension with a cell density of $5\times10^4$/mL. Plate 200 μl of the cell suspension into each well of a 96-well plate and cultivate in an environment of 37° C. and 5% CO$_2$ in an incubator. The sample is added after the cells are attached.

2) Add 100 μL of ligand-modified CuNCs samples or ligand-modified copper nanoparticles samples with different particle sizes, which are prepared using maintenance medium to make the final concentration being 0.1 ppm, 1 ppm, 5 ppm, 10 ppm and 20 ppm, respectively. After 2 hours of pretreatment with ligand-modified CuNCs, the different groups of cells were added with MPP$^+$ (final concentration is 1 mM). A blank control that did not contain SH-sy5y cells, a negative control group containing SH-sy5y cells but without CuNCs and MPP$^+$, a cell control group containing SH-sy5y cells and 1 mM MPP$^+$ only, a sample control group containing SH-sy5y cells and 100 ppm CuNCs but without MPP$^+$, and a ligand control group containing SH-sy5y cells and 1 mM MPP$^+$ and corresponding ligand molecules (final concentration is 20 ppm) were set. Then the cells were cultured at 37° C. for 24 h. After centrifugation to remove the culture medium, 100 μL maintenance medium containing 10% CCK-8 were added to each well, and then incubate for 4 h. The absorbance of each well was then measured at 450 nm. The absorbance could reflect the pre-protective and curative effects of ligand-modified CuNCs against MPP$^+$ lesion.

Figure 14:
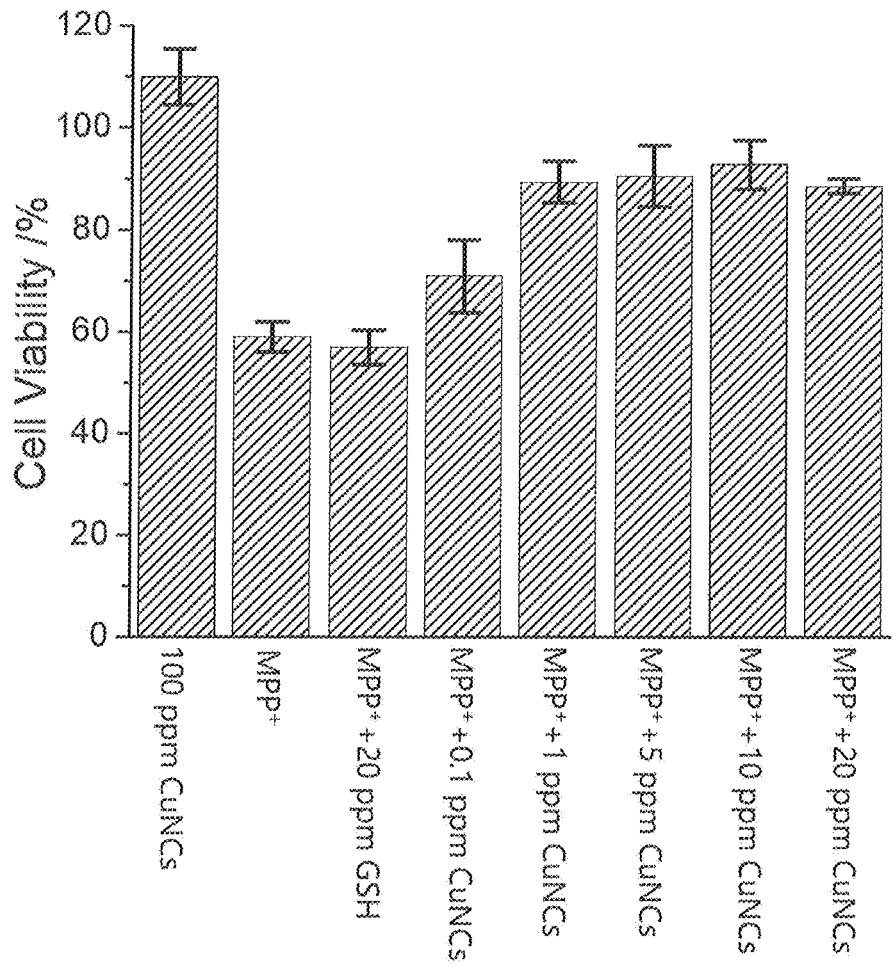
FIG. 14 provides bar graphs showing the effect of CuNCs on the cell viability of $MPP^+$-lesioned PD cell (SH-sy5y) model.

Referring now to FIG. 14, there are provided bar graphs showing the effect of CuNCs on the cell viability of MPP$^+$-lesioned PD cell (SH-sy5y) model. The results indicate that after 24 h of cultivation, the cell viability of the sample control group added with 100 ppm CuNCs, but not treated with MPP$^+$ increases to 110.0±6.2% relative to the blank control group (set as 100%) ($P<0.01$), suggesting that CuNCs are nontoxic. The cell viability of the model control group added with 1 mM MPP$^+$ but without CuNCs decreases to 58.9±5.4% ($P<0.01$, v.s. the blank control group), the cell viability of the ligand control group is 56.9±3.4% ($P<0.01$, v.s. the blank control group), suggesting that ligand alone does not raise the viability of MPP$^+$ lesioned cells. While the cell viability of the administration groups which were added with 0.1 ppm, 1 ppm, 5 ppm, 10 ppm and 20 ppm of CuNCs increases to 70.9±7.1% ($P<0.001$, v.s. the model control group), 89.3±4.1% ($P<0.001$, v.s. the model control group), 90.5±6.1% ($P<0.001$, v.s. the model control group), 92.8±4.8% ($P<0.001$, v.s. the model control group) and 88.5±1.4% ($P<0.001$, v.s. the model control group). The results suggest that the ligand-modified CuNCs provided by the present invention have a significant protective effect on nerve cells in PD, and this effect is due to CuNCs other than the ligand.

The same steps are also adopted to carry out the experiments for the CuNCs modified with other ligands, e.g. L(D)-cysteine, N-isobutyryl-L(D)-cysteine (L(D)-NIBC) and N-acetyl-L(D)-cysteine (L(D)-NAC). The effect is similar and will not be described in detail.

(14) Characterization of CuNCs

CuNCs modified with one or more ligands were synthesized. The ligands include thymine, L(D)-cysteine and other cysteine derivatives such as N-isobutyryl-L-cysteine (L-NIBC), N-isobutyryl-D-cysteine (D-NIBC), N-acetyl-L-cysteine and N-acetyl-D-cysteine, cysteine-containing oligopeptides and their derivatives including, but not limited to, dipeptides, tripeptide, tetrapeptide and other peptides containing cysteine, such as L-cysteine-L-arginine dipeptide (CR), L-arginine-L-cysteine dipeptide (RC), L-cysteine L-histidine (CH), glycine-L-cysteine-L-arginine tripeptide (GCR), L-proline-L-cysteine-L-arginine tripeptide (PCR), L-glutathione (GSH), glycine-L-serine-L-cysteine-L-arginine tetrapeptide (GSCR) and glycine-L-cysteine-L-serine-L-arginine tetrapeptide (GCSR), and other thiol-containing compounds, such as one or more of 1-[(2S)-2-methyl-3-thiol-1-oxopropyl]-L-proline, thioglycollic acid, mercaptoethanol, thiophenol, D-3-trolovol and dodecyl mercaptane.

The following are characterization data of GSH modified CuNCs are shown in following as an example.

1) Observation of the Morphology by Transmission Electron Microscope (TEM)

The test powders (GSH modified CuNCs sample) were dissolved in ultrapure water to 2 mg/L as samples, and then test samples were prepared by hanging drop method. The specific method: 5 μL of the samples were dripped on the copper mesh, volatized naturally till the water drop disappeared, and then observe the morphology of the samples by JEM-2100F STEM/EDS field emission high-resolution TEM.

Figure 15:
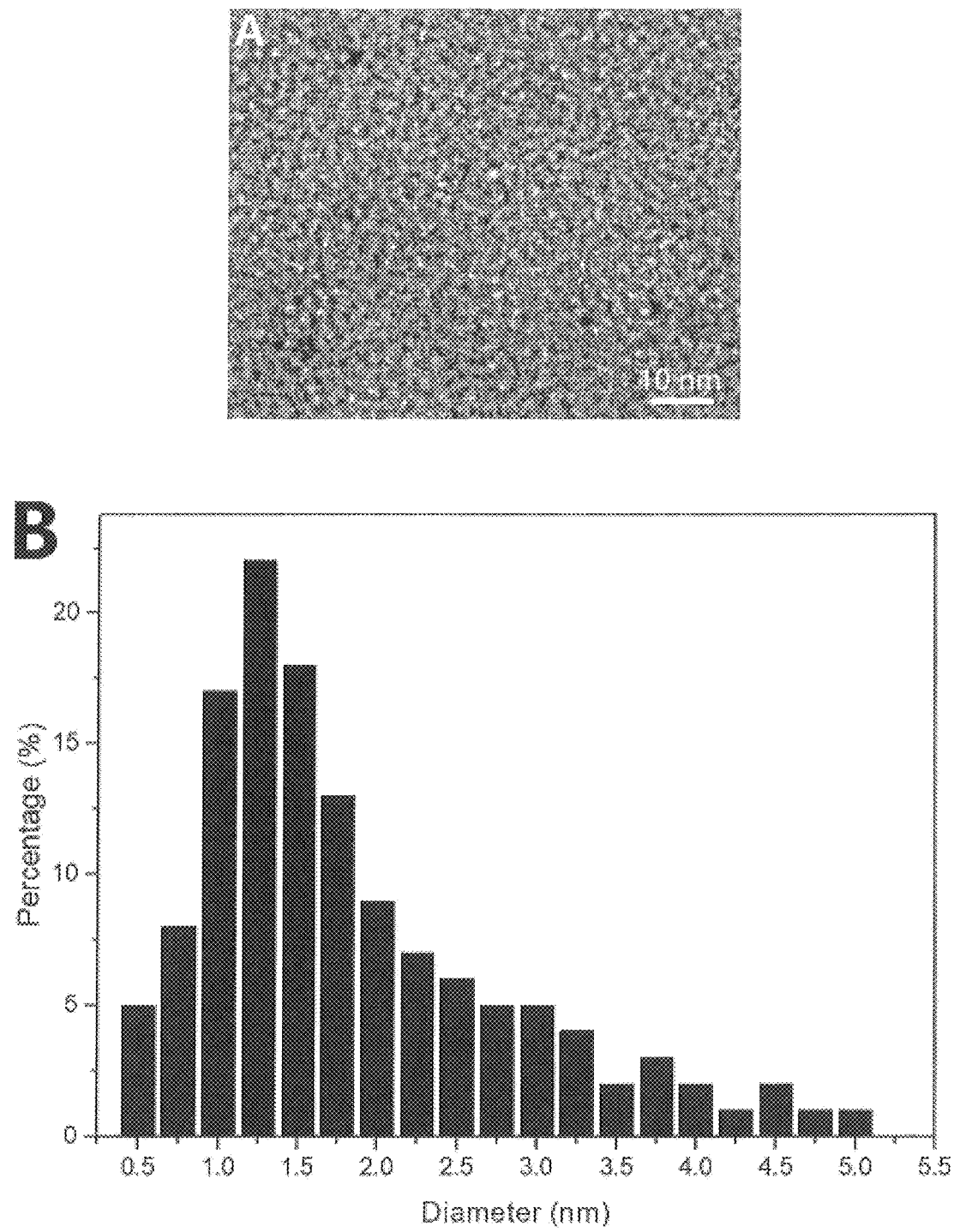
FIG. 15 shows characterization data of CuNCs. (A) A typical transmission electron microscopic (TEM) image of CuNCs. (B) Size distribution of CuNCs calculated from TEM images. (C) X-ray photoelectron spectroscopy (XPS) spectrum of $2p_{3/2}$ and $2p_{1/2}$ electrons of Cu(0) in CuNCs. (D) Comparison between Fourier transform infrared (FT-IR) spectroscopies of GSH modified CuNCs (upper) and GSH (lower). (E) Fluorescent excitation (left) and emission spectra (right) of CuNCs.
Figure 15:
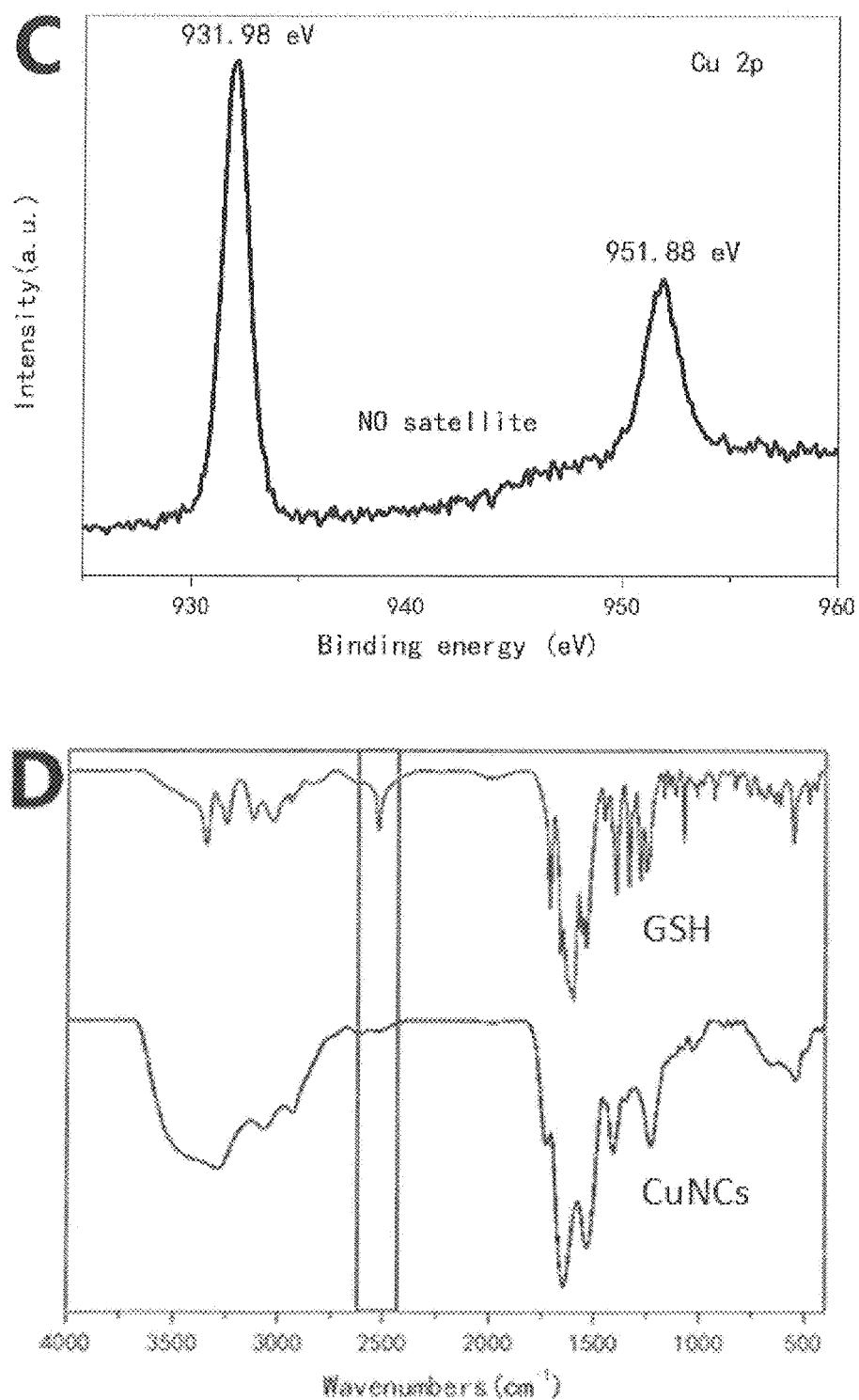
Figure 15:
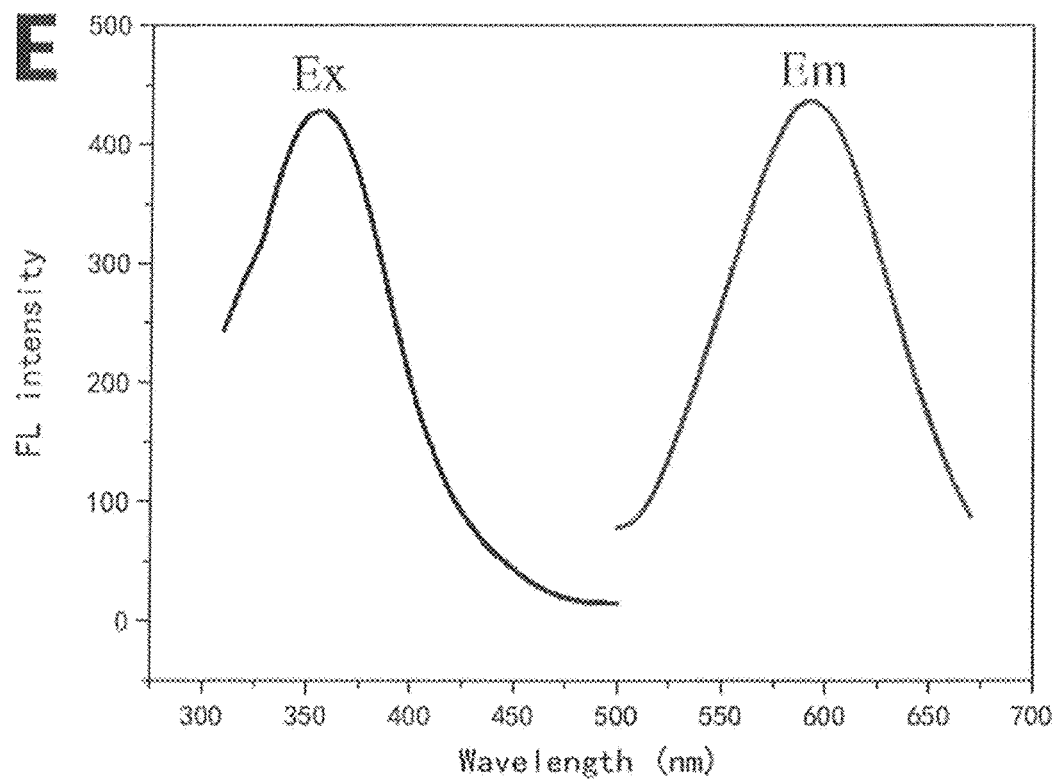

Panel A and panel B of FIG. 15 show a typical SEM image of GSH modified CuNCs, and their size distribution was calculated from different TEM images. It indicates that CuNCs are well-dispersed and their sizes lie in a range of 0.5-5.0 nm.

2) X-Ray Photoelectron Spectroscopy

The X-ray photoelectron spectroscopy (XPS) spectra was measured on an ESCALAB 250Xi X-ray photoelectron spectrometer. A double-sided conductive adhesive (3 mm×3 mm) was attached to the aluminum foil, the test powder was evenly spread on the double-sided tape and covered with a layer of aluminum foil. The sample was kept under a pressure of 8 MPa for one minute. Remove the residual powder on the surface and then the center sample (1 mm×1 mm) was cut out for XPS testing.

Panel C of FIG. 15 is the XPS spectrum of Cu element in CuNCs. Two peaks appear at 931.98 and 951.88 eV, which can be ascribed to the binding energies of the $2P_{3/2}$ and $2p_{1/2}$ electrons of Cu, respectively. The absence of Cu $2p_{3/2}$ satellite peak around 942.0 eV confirms that the Cu(II) electrons are not present. As the binding energy of Cu(0) is only 0.1 eV away from that of Cu(I), it is not possible to exclude the formation of Cu(I), and the valence state of Cu in the obtained GSH modified CuNCs most likely lies between 0 and +1.

3) Fourier Transform Infrared (FT-IR) Spectroscopy

The FT-IR spectra was tested on the PerkinElmer LS 55 fluorescence spectrometer. The test powder was dissolved in ultrapure water, and measured at room temperature. The scanning range was 200-800 nm, the sample cell was a standard quartz cuvette with an optical path of 1 cm.

Panel D of FIG. 15 shows a comparison between FT-IR spectroscopies of GSH modified CuNCs (upper) and GSH (lower). GSH exhibits a number of characteristic IR bands, i.e., COOH$^-$ (1,390 and 1,500 cm$^{-1}$), the N—H stretch (3,410 cm$^{-1}$), and the N—H bending (1,610 cm$^{-1}$) of NH$_2$ group. The peak observed at 2,503 cm$^{-1}$ can be assigned to the S—H stretching vibrational mode. Corresponding characteristic IR bands can all be found for GSH modified CuNCs, except for the S—H stretching vibration band (2,503 cm$^{-1}$). It suggests the cleavage of the S—H bond and the binding of the GSH molecules to the surface of CuNCs through the formation of Cu—S bond.

4) Fluorescence Spectroscopy

The test powder was dissolved in ultrapure water, and measured by fluorescence spectroscopy at room temperature.

As shown in the panel E of FIG. 15, the CuNCs exhibit red emission with a peak at 595 nm and a corresponding full width at half maximum (FWHM) of approximately 80 nm under the excitation peak at 365 nm. It is worth noting that the FL intensity of the CuNCs will be significant improved when the ethanol was added to the solution due to the aggregation induced emission enhancement. In addition, the large stokes shift (230 nm) indicated good prospects for fluorescent probes and bioimaging.

(15) CAT Activity of CuNCs

At present, the detection of CAT activity is only characterized by the ultraviolet absorption intensity of hydrogen peroxide at 240 nm by ultraviolet absorption. However, since the synthesized copper clusters may change after catalyzing the $H_2O_2$ process, the ultraviolet absorption is greatly increased below 300 nm. Therefore, the experiment verified the catalytic effect of CuNCs by observing the oxygen produced from $H_2O_2$ catalyzed by CuNCs. The experiment is to observe the bubbles generated by the decomposition of $H_2O_2$, thus, the experimental phenomenon is more obvious with higher concentration of $H_2O_2$. The experimental procedure was as follows.

Figure 16:
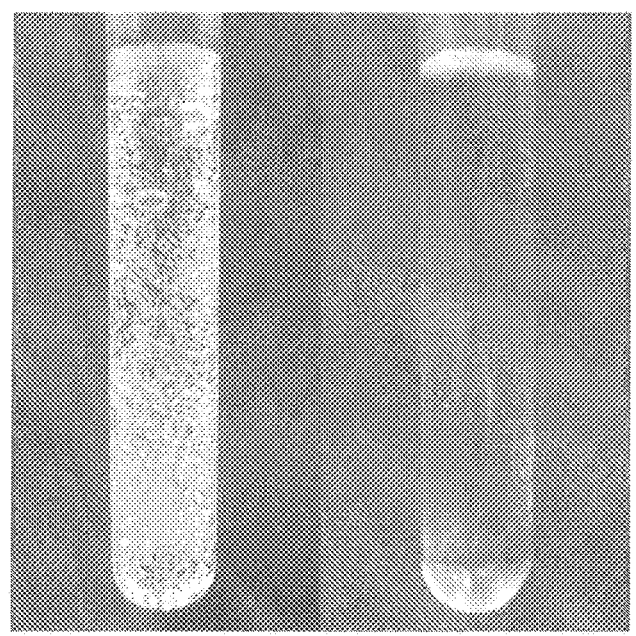
FIG. 16 shows CAT activities of CuNCs.

At room temperature, 4 ml of a 10% $H_2O_2$ solution was added to the test tube, and then 2 ml of a 2000 ppm CuNCs solution was added and catalyzed for 3 minutes. As shown in FIG. 16, the left test tube was a test tube to which the CuNCs was added, and on the tube wall had a large amount of $O_2$ bubbles that were produced by catalytical decomposition of $H_2O_2$; the right side is a control group with an equal volume of ultrapure water being added, which had no obvious bubbles. Experiments showed that CuNCs had excellent catalase activity.

(16) GPx Activity of CuNCs

The GPx activity of copper clusters was studied by 5,5'-dithiobis-(2-nitrobenzoic acid) (DTNB) chromogenic assay. GPx promotes the reaction of hydrogen peroxide with reducing glutathione (GSH) to form water and oxidized glutathione (GSSG). The thiol-containing compound can react with DTNB to cleave the disulfide bond of DTNB to produce 2-nitro-5-thiobenzoic acid ($NTB^-$), which can be ionized in water under neutral or alkaline pH conditions to form $NTB^{2-}$ bivalence anion. $NTB^{2-}$ can be quantified by measuring the absorbance at 412 nm, thereby quantifying the amount of GSH in the reaction.

The experimental procedure was as follows.

The following reagents were sequentially added to the test tubes at room temperature:
(1) 0.2 ml of a certain concentration of CuNCs solution (an appropriate amount of CuNCs was dissolved in PBS buffer);
(2) 0.5 ml GSH (1 mM) (an appropriate amount of GSH powder was dissolved in PBS buffer);
(3) 0.5 ml $H_2O_2$ solution (1.5 mM);
(4) 0.2 ml of DTNB (1 mM) containing 1% sodium citrate (0.3 g of trisodium citrate dihydrate was dissolved in 30 ml of PBS buffer, and DTNB was dissolved therein, and sonication was performed).

The solutions were mixed by gently shaking the test tubes to detect the UV spectrum.

In the blank group, the CuNCs solution was replaced with 0.2 ml PBS buffer; the experimental groups studied the catalytic effect by changing the concentration of copper clusters and catalytic time.

Figure 17:
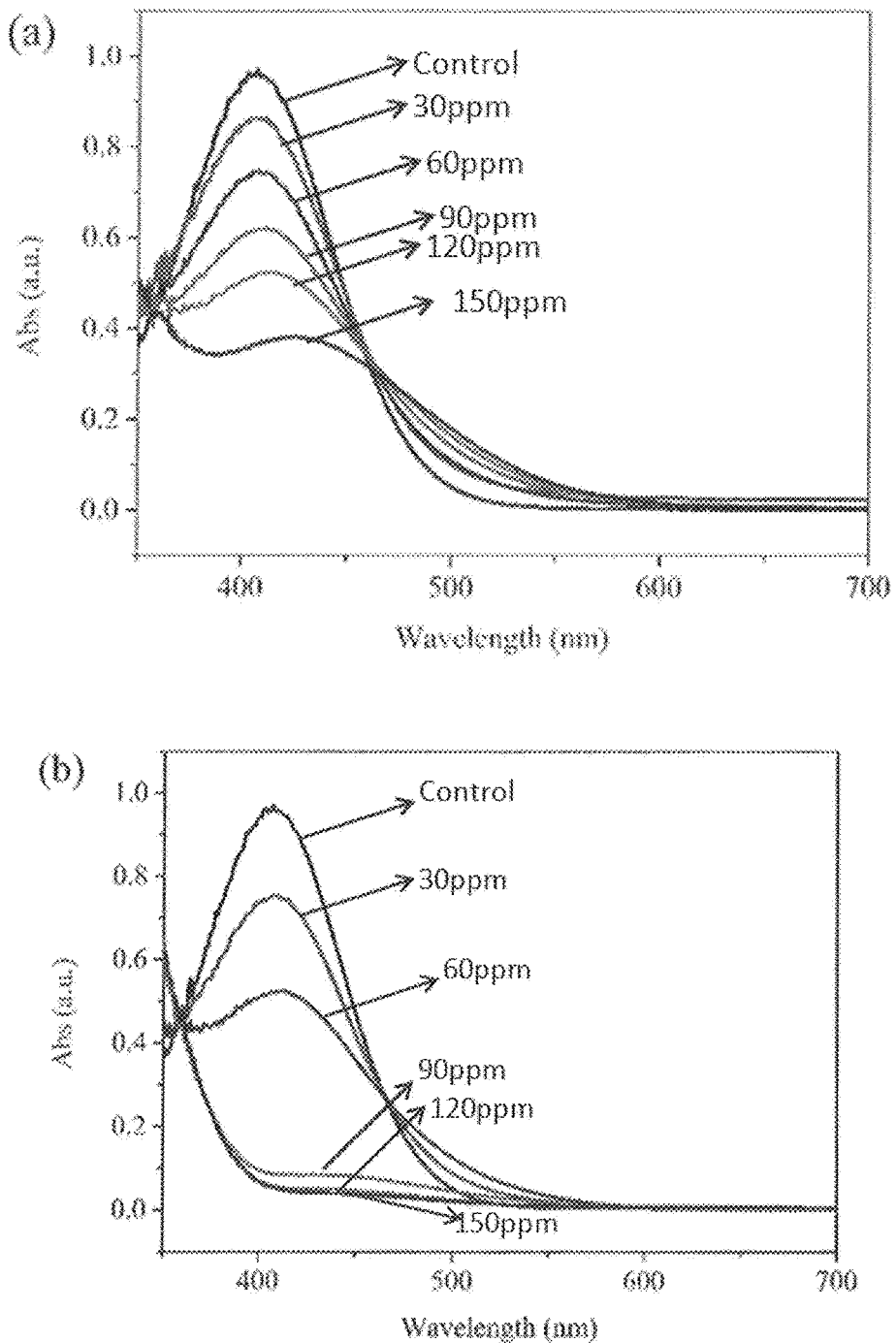
FIG. 17 shows GPx activities of CuNCs.
Figure 17:
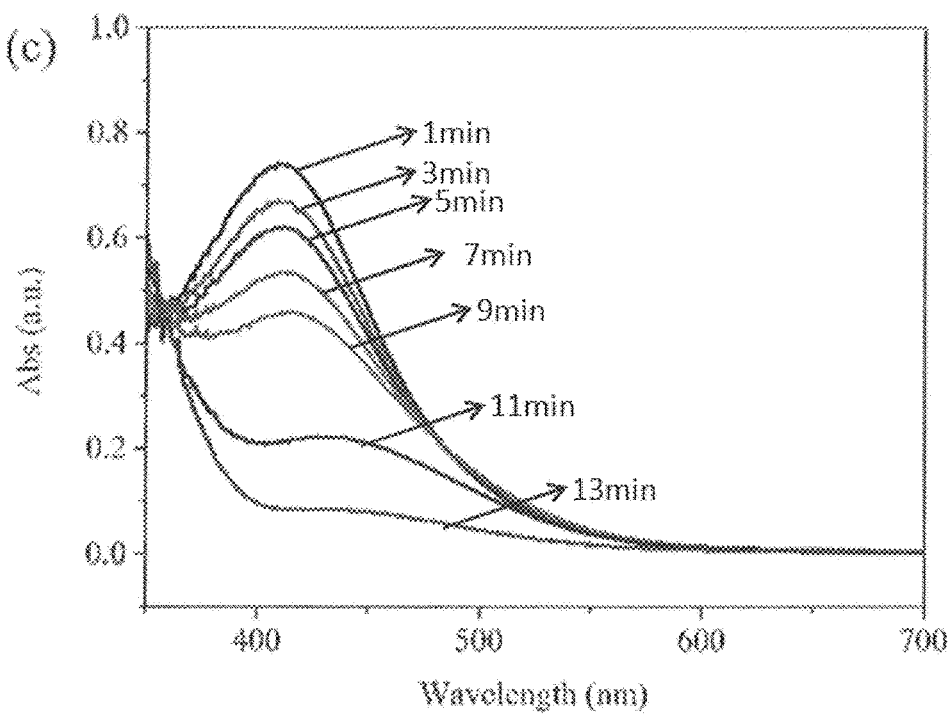

FIG. 17a shows the experimental results obtained by catalyzing for 5 minutes at room temperature for different concentrations of copper clusters (30 ppm, 60 ppm, 90 ppm, 120 ppm, 150 ppm). It was found that the UV absorption at 412 nm decreased significantly with the increase of catalyst concentration, indicating that the GSH in the system decreased with the increase of catalyst concentration; this also means that with the increase of catalyst, more $H_2O_2$ oxidized GSH.

To observe the results of subsequent experiments, the reaction time was extended. FIG. 17b shows the results after 13 minutes of catalysis. With copper cluster concentrations of 30 ppm and 60 ppm, the UV absorption continued to decrease, indicating continuing catalytic reaction; in the meantime, with the copper nanoclusters concentration of 90 ppm or more, the UV absorption was almost stopped, indicating that GSH was almost completely catalyzed. Therefore, 90 ppm was selected for continuous monitoring.

FIG. 17c shows that the catalysis was slower at the beginning, the catalytic rate gradually increased as the reaction progressed, and the catalytic reaction was almost completed at 11 to 13 minutes.

(17) SOD Activity of CuNCs

The SOD activity assay was determined by using a superoxide dismutase (SOD) assay kit (Nanjing Jiancheng Bio). In short, *Astragalus* and Xanthine oxidase react to produce superoxide, further reducing WST-1(2-(4-iodophenyl)-3-(4-nitrophenyl)-5-(2,4-Diphenyl)-2H-tetrazolium); the produced formazan is detected in the ultraviolet spectrum at 440 nm. The SOD activity was judged by adding copper clusters to observe the decrease in ultraviolet absorption at 440 nm.

Preparation of the substrate working solution: substrate stock solution:buffer solution was mixed at a ratio of 1:200 to form the substrate working solution, which was currently used.

Preparation of enzyme working solution: enzyme stock solution:enzyme dilution solution was mixed in a ratio of 1:10 to prepare the enzyme working solution, which was currently used.

The experiment groups were setup as follows:

|  | Control well | control blank well | Assay well | Detection blank well |
| --- | --- | --- | --- | --- |
| Test sample(μL) | — | — | 20 | 20 |
| Distilled water(μL) | 20 | 20 | — | — |
| Enzyme working solution (μL) | 20 | — | 20 | — |
| Enzyme dilution solution (μL) | — | 20 | — | 20 |
| Substrate working solution (μL) | 200 | 200 | 200 | 200 |

According to the above setup, wells in a 96-well plate were sequentially added: (1) substrate working solution; (2) enzyme dilution solution; (3) test sample or distilled water; and (4) enzyme working solution. Mixed well, incubated in a microplate reader at 37° C., and read the UV absorbance at 450 nm.

Figure 18:
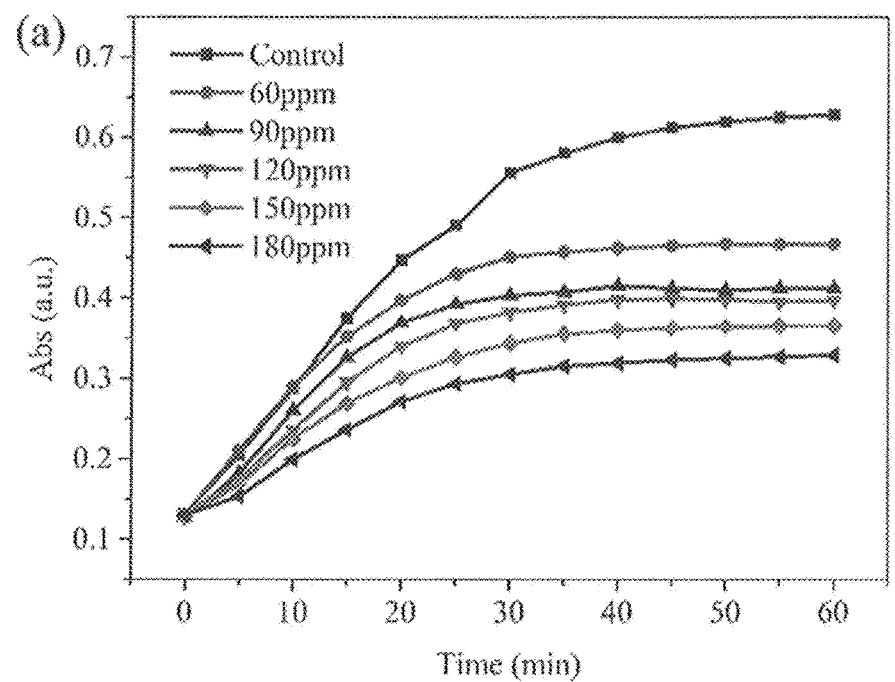
FIG. 18 shows SOD activities of CuNCs.
Figure 18:
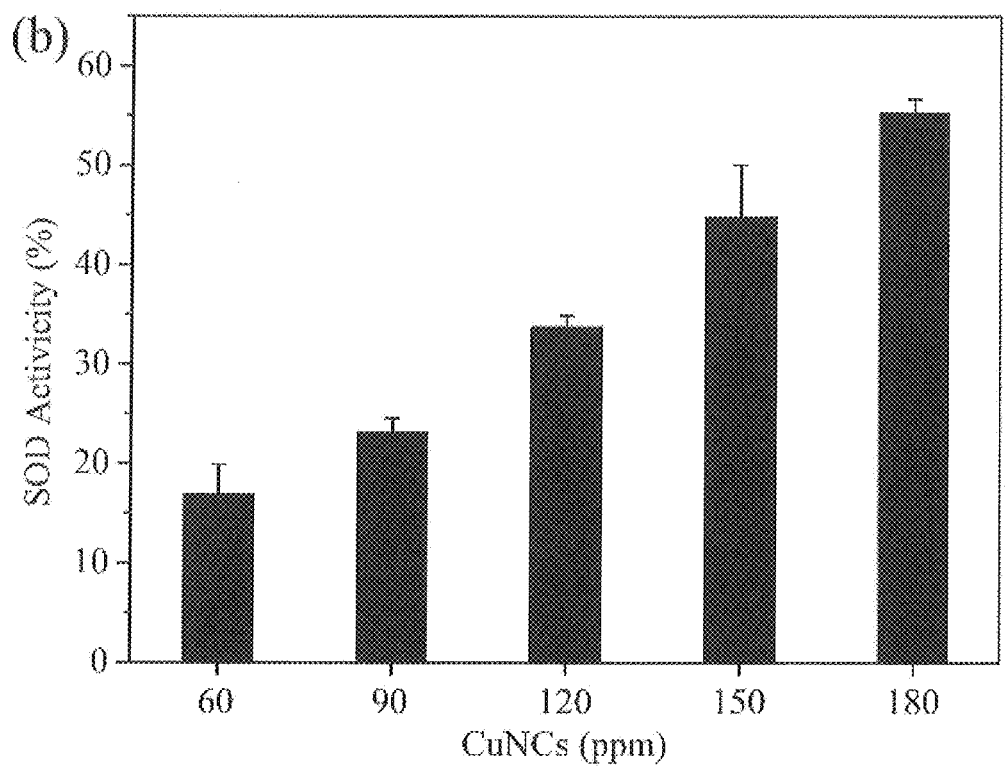

FIG. 18a shows the UV absorbance at 45 nm during incubation of 60 minutes with different concentrations of CuNCs. As shown in FIG. 18a, the UV absorption value decreased gradually during the incubation period as the concentration of CuNCs added increased, and the UV absorption value for each dose of CuNCs was plateaued after 30 minutes; these demonstrated that CuNCs had excellent SOD activity, and its SOD activity was increased with increasing concentrations of CuNCs. In light of the above results, the UV absorption value at the incubation time of 20 min was selected to calculate the SOD inhibition rate. As shown in FIG. 18b, the SOD inhibition rates of CuNCs at 60 ppm, 90 ppm, 120 ppm, 150 ppm, and 180 ppm were 16.9%, 23.2%, 33.7%, 44.8%, and 55.2%, respectively. The SOD activity refers to the amount of enzyme corresponding to a SOD activity unit when the SOD inhibition rate reaches 50% in the reaction system. Therefore, taken 150 ppm CuNCs as an example, it has a SOD activity of 10.24 U/mg.

The experimental results show that the synthesized GSH-CuNCs have the enzymatic activities of three main antioxidant enzymes with different structures and functions: catalase (CAT), glutathione peroxidase (GPx) and superoxide dismutase (SOD).

(18) $H_2O_2$-Induced Glaucoma Cell (RGC-5) Model

In this embodiment, the cell viability was used as an indicator to test the effects of ligand-modified copper nanoclusters (CuNCs) on the cytotoxicity induced by $H_2O_2$; the results from the cck-8 assay demonstrated that CuNCs have neuroprotective effects against oxidative stress-induced damages in retinal ganglion cells (RGC).

RGC-5 cells in logarithmic growth phase were diluted with complete medium (DMEM medium+10% FBS+1% penicillin-streptomycin) into a cell suspension with a density of $5\times10^4$/mL, inoculated with 100 μL per well in 96-well plates. The cells were cultured at 37° C. in a 5% $CO_2$ incubator. After the cells were attached, the original culture solution was discarded, and 50 μL of different concentrations of CuNCs prepared from maintenance medium (DMEM medium+2% FBS+1% penicillin-streptomycin) were added to different wells. The final concentrations were 0.5, 5 and 20 ppm respectively (i.e. groups 5, 6, 7 respectively in FIG. 19). After pretreatment for 2 h, about 50 μL of $H_2O_2$ (final concentration of 105 μM) was added. The cells were incubated for 24 h, and 10% CCK-8 was added to each well for 4 h. The absorbance values of the respective wells were measured at the wavelength of 450 nm to evaluate the protection effect of CuNCs against $H_2O_2$-induced damages. In the above experiments, provided were a blank control group in which cells were not treated, a model control group in which cells were treated with 105 μM $H_2O_2$, a CuNCs control group in which 100 ppm of CuNCs were added but no $H_2O_2$ was added, and a ligand control group in which 20 ppm ligand and 105 μM $H_2O_2$ were added (i.e. groups 1, 2, 3, 4 respectively in FIG. 19).

Figure 19:
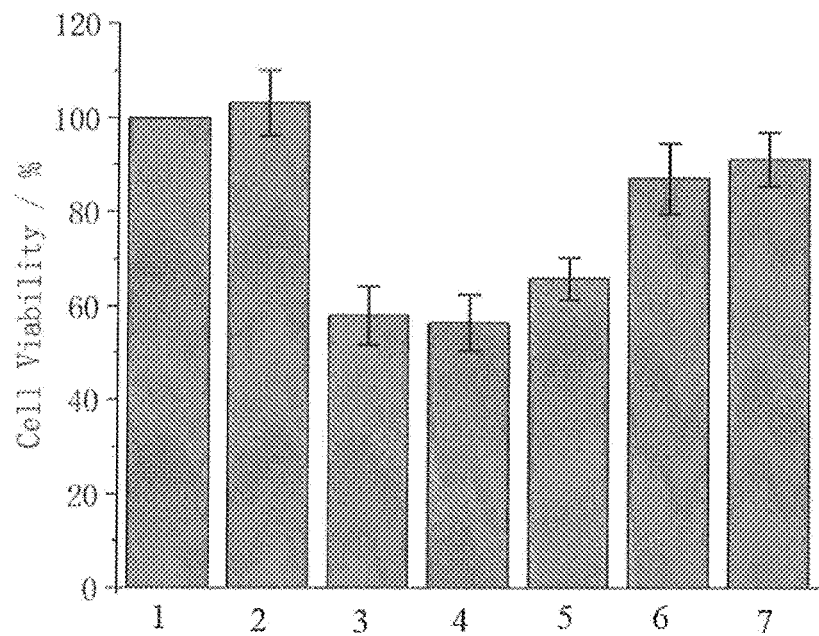
FIG. 19 is a bar graph showing the effect of CuNCs on the cell viability in the $H_2O_2$-induced glaucoma cells (RGC-5) model.

The experimental results of GSH-modified CuNCs are taken as an example, as shown in FIG. 19. The results showed that after 24 hours of culture, the cell viability of the copper cluster control group (i.e. group 2) supplemented with 100 ppm CuNCs but not treated with $H_2O_2$ was 103.2±7.0% relative to the blank control group (i.e. group 1) (100%) (P>0.05), indicating that the CuNCs was non-toxic. The cell viability of the model control group (i.e. group 3) added with 100 μM $H_2O_2$ but with no CuNCs was reduced to 58.0±6.2% of the blank control group (P<0.005). The cell viability of the ligand control group (i.e. group 4) added with 20 ppm of GSH and 100 μM of $H_2O_2$ was 56.5±5.9% of the blank control group (P<0.01 for the comparison with the blank control group and P>0.05 for the comparison with the model control group), indicating that the ligand when used alone did not increase the cell viability in the $H_2O_2$-induced damage cell model. The cell viability of the administration groups with 0.5 ppm (i.e. group 5), 5 ppm (i.e. group 6) and 20 ppm (i.e. group 7) CuNCs increased to 65.9±4.5% (P<0.05 for comparison with the model control group), 87.1±7.4% (P<0.01 for comparison with the model control group), and 91.2±5.7% (P<0.01 for comparison with the model control group).

The above results indicate that the CuNCs of the present invention can significantly improve the cell viability in the $H_2O_2$-induced damage RGC cell model, indicating that it can resist the apoptosis of RGC cells induced by oxidative stress, while GSH had no apparent effect on the apoptosis of RGC cells induced by oxidative stress.

Other ligand-modified CuNCs have also been tested following the same steps, and have similar effects, which will not be repeated here.

(19) Multiple Sclerosis (MS) Mouse Model

Experimental autoimmune encephalomyelitis (EAE) is a classical animal model corresponding to MS, which is mainly mediated by $CD4^+$ T cells. When antigen-sensitized $CD4^+$ T cells cross the blood-brain barrier and enter the central nervous system, they induce an immune response to their own myelin antigen, resulting in immune damage to the brain and spinal cord. Since myelin oligodendrocyte glycoprotein (MOG) is present in the outermost layers of myelin membranes and oligodendrocytes, it is highly immunogenic, and there is evidence that anti-MOG antibodies play an important role in the pathogenesis of MS. Therefore, we induced the EAE model by immunizing C57BL/6 mice with MOG35-55.

(1) Materials 10 weeks-old 18 female C57BL/6 mice, purchased from Wuhan Wanqian Jiaxing Biotechnology Co., Ltd. Hooke Kit™ MOG35-55/CFA Emulsion PTX Kit (Cat. No. EK-2110), purchased from Hooke Laboratories (USA).

(2) EAE Model Establishment a. Mice were subcutaneously injected of antigen emulsifier twice in different body sites (Hooke Kit™ MOG35-55/CFA Emulsion PTX kit), 0.1 ml per site; 0.2 ml for each mouse.

b. After 2 hours, PTX toxin (Hooke Kit™ MOG35-55/CFA Emulsion PTX kit) was first injected. Each mouse was injected intraperitoneally with 0.1 ml of PTX toxin.

c. After 24 hours, each mouse was repeatedly injected with PTX toxin once.

PTX toxin (PTX in the kit was dissolved in glycerol at a concentration of 200 ng/ul; it should be dissolved in PBS solution when used, freshly prepared each time, and used within 2 hours after dispensing) was prepared as follows:

1) First, calculated the volume of PBS solution required for the injection based on the number of mice used in the experiment. Generally, one mouse was assumed to need 0.12 ml of PBS solution. The required PBS solution was then added to a 50 ml test tube.

2) Then calculated the required dose of PTX toxin. Typically, 80 ng of PTX is required for each injection of each mouse. The total amount of PTX required was then calculated based on the number of mice used in the experiment.

PTX(ul)=number of mice*PTX dose*1.2/200 ng/ul
(PTX concentration in the kit).

3) The PTX was then placed in a 50 ml tube containing PBS for dissolution.

(3) Experiments

18 C57BL/6 mice were randomly divided into three groups (n=6): model control group with administration of PTX only, treatment group with co-adminstion of PTX and CuNCs, and normal control group, 6 rats in each group. For the treatment group, copper cluster drugs were administered at a dose of 30 ppm once a day by injection of the tail vein on the day of the start of modeling. For the normal control group, normal mice were injected with the same volume of physiological saline as the copper cluster solution per day.

Mice were observed daily and scored for neurological functions. The scoring criteria were: 0 point, hind limb extension, tail extension, normal gait; 1 point, hind limb extension, tail tension disappeared, normal gait; 1.5 points, tail drooping, hind limb movement was abnormal; 2 points, both hind legs are weak, the mouse gait is uncoordinated, the tail is drooping; 2.5 points, the tail is drooping, and the hind limbs are dragged; 3 points, double hind limb paralysis, tail drooping; 4 points, double hind limb paralysis, forelimb paralysis or muscle weakness, tail drooping; 5 points, no movement, no response to the touch, respiratory changes, sudden death or death.

(4) Results

Figure 20:
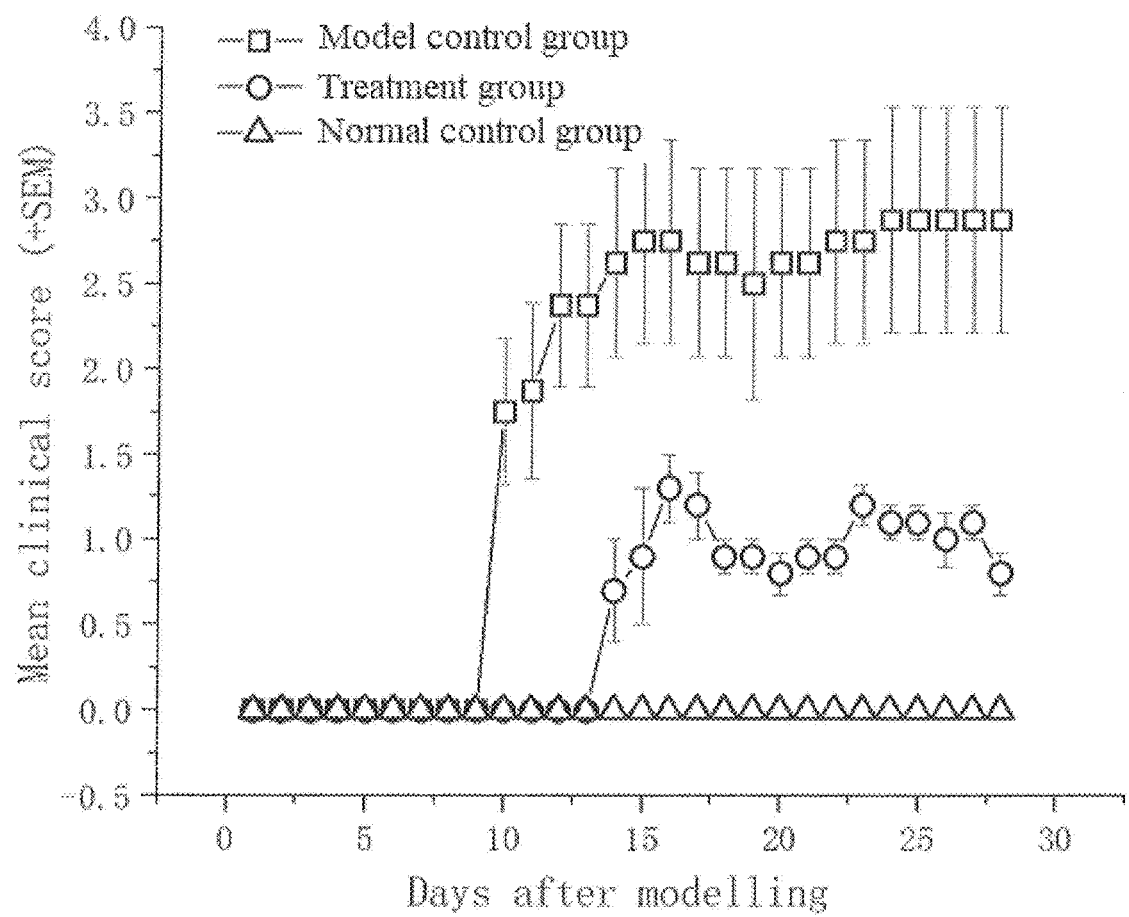
FIG. 20 is a graph showing the effect of GSH-modified copper clusters (CuNCs) on the motor behavior of a multi-sclerosis mouse model modeled by EAE.

FIG. 20 is a graph showing the effect of GSH-modified copper clusters (CuNCs) on the motor behavior of a multi-sclerosis mouse model modeled by EAE. As shown in FIG. 20, the model control group began to have obvious dyskinesia on the 10th day, and the sputum appeared on the lower limbs on the 13th to 14th day, but the normal control group did not show significant changes in the exercise ability at the end of the experiment, indicating that the model was successful. The treatment group showed symptoms of slight sagging of the tail on the 14th day, but the exercise ability did not show significant difference until the end of the experiment and normal mice, indicating that the CuNCs drug has a significant protective effect on the motor behavior of the EAE mouse model, and can be used for the prevention and treatment of multiple sclerosis.

Other ligand-modified CuNCs were also tested using the same procedure, such as L(D)-cysteine, N-isobutyryl-L(D)-cysteine (L(D)-NIBC) and N-acetyl-L(D)-cysteine (L(D)-NAC). The effects are similar, so they will not be described in detail here.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

REFERENCES

Adamczyk B, Adamczyk-Sowa M. New Insights into the Role of Oxidative Stress Mechanisms in the Pathophysiology and Treatment of Multiple Sclerosis. Oxid Med Cell Longev. 2016:1973834. Epub 2016 Oct. 18.

Jin R, et al. Atomically Precise Colloidal Metal Nanoclusters and Nanoparticles: Fundamentals and Opportunities, *Chem. Rev.,* 2016, 116, 10346-10413

Kim G H, et al. The Role of Oxidative Stress in Neurodegenerative Diseases, *Exp Neurobiol.* 2015, 24(4): 325-340

Liu X, et al. Atomically Precise Copper Nanoclusters and Their Applications, *Coord. Chem. Rev.,* 2018, 359, 112-126

Ohl K, Tenbrock K, Kipp M. Oxidative stress in multiple sclerosis: Central and peripheral mode of action. Exp Neurol. 2016; 277:58-67.

Yao Q, et al. Toward Total Synthesis of Thiolate-Protected Metal Nanoclusters, *Acc. Chem. Res.;* 2018; 51; 1338-1348

The invention claimed is:

1. A method of treating multiple sclerosis in a subject, said method comprising:
   administering a composition to the subject with the multiple sclerosis;
   wherein said composition comprises copper nanoclusters;
   wherein said copper nanoclusters comprise a ligand; and
   wherein the ligand-modified copper nanoclusters have a diameter in the range of 0.5-5 nm.

2. The method of claim 1, wherein the ligand-modified copper nanoclusters have a diameter in the range of 0.5-3 nm.

3. The method of claim 1, wherein the ligand-modified copper nanoclusters have a diameter in the range of 0.5-2.5 nm.

4. The method of claim 1, wherein the ligand is one selected from the group consisting of thymine, thymine-modified hyaluronic acid, L-cysteine and its derivatives, D-cysteine and its derivatives, cysteine-containing oligopeptides and their derivatives, and other thiol-containing compounds.

5. The method of claim 4, wherein the L-cysteine and its derivatives are selected from the group consisting of L-cysteine, N-isobutyryl-L-cysteine, and N-acetyl-L-cysteine, and wherein the D-cysteine and its derivatives are selected from the group consisting of D-cysteine, N-isobutyryl-D-cysteine, and N-acetyl-D-cysteine.

6. The method of claim 4, wherein the cysteine-containing oligopeptides and their derivatives are cysteine-containing dipeptides, cysteine-containing tripeptides or cysteine-containing tetrapeptides.

7. The method of claim 6, wherein the cysteine-containing dipeptides are selected from the group consisting of L-cysteine-L-arginine dipeptide, L-arginine-L-cysteine dipeptide, L-histidine-L-cysteine dipeptide, and L-cysteine-L-histidine dipeptide.

8. The method of claim 6, wherein the cysteine-containing tripeptides are selected from the group consisting of glycine-L-cysteine-L-arginine tripeptide, L-proline-L-cysteine-L-arginine tripeptide, L-lysine-L-cysteine-L-proline tripeptide, and L-glutathione.

9. The method of claim 6, wherein the cysteine-containing tetrapeptides are selected from the group consisting of glycine-L-serine-L-cysteine-L-arginine tetrapeptide, and glycine-L-cysteine-L-serine-L-arginine tetrapeptide.

10. The method of claim 4, wherein the other thiol-containing compounds are selected from the group consisting of 1-[(2S)-2-methyl-3-thiol-1-oxopropyl]-L-proline, thioglycollic acid, mercaptoethanol, thiophenol, D-3-trolovol, N-(2-mercaptopropionyl)-glycine, and dodecyl mercaptan.

* * * * *